US012788972B2

(12) United States Patent
Deer

(10) Patent No.: US 12,788,972 B2
(45) Date of Patent: Nov. 10, 2026

(54) DORSAL ROOT GANGLIA SURGICAL LEADS

(71) Applicant: Advanced Neuromodulation Systems, Inc., Plano, TX (US)

(72) Inventor: Timothy R. Deer, Charleston, WV (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 109 days.

(21) Appl. No.: 18/917,565

(22) Filed: Oct. 16, 2024

(65) Prior Publication Data

US 2025/0032785 A1 Jan. 30, 2025

Related U.S. Application Data

(60) Continuation of application No. 17/893,358, filed on Aug. 23, 2022, now Pat. No. 12,121,717, which is a (Continued)

(51) Int. Cl.

| | |
|---|---|
| ***A61N 1/05*** | (2006.01) |
| ***A61N 1/06*** | (2006.01) |
| ***A61N 1/36*** | (2006.01) |

(52) U.S. Cl.

CPC ....... *A61N 1/0553* (2013.01); *A61N 1/36071* (2013.01); *A61N 1/36178* (2013.01); *A61N 1/0558* (2013.01); *A61N 1/06* (2013.01)

(58) Field of Classification Search

CPC ................ A61N 1/0551; A61N 1/0553; A61N 1/36071; A61N 1/36178; A61N 1/0558; A61N 1/06

See application file for complete search history.

(56) References Cited

U.S. PATENT DOCUMENTS

| | | | |
|---|---|---|---|
| 7,006,875 | B1 | 2/2006 | Kuzma et al. |
| 8,244,374 | B1 | 8/2012 | Swanson |

(Continued)

FOREIGN PATENT DOCUMENTS

| | | |
|---|---|---|
| WO | WO-2008091197 A1 | 7/2008 |
| WO | WO-2011072128 A1 | 6/2011 |
| WO | WO-2014209877 A1 | 12/2014 |

OTHER PUBLICATIONS

Australian Examination Report No. 1, AU2017352214, dated Jun. 21, 2019.

(Continued)

*Primary Examiner* — Paula J Stice

(74) *Attorney, Agent, or Firm* — Carroll, Hoette & Butscher, LLC; Christopher R. Carroll

(57) ABSTRACT

Implementations described and claimed herein provide paddle leads for dorsal root ganglia (DRG) stimulation and methods of implanting the same. In one implementation, the paddle lead has a small profile facilitating deployment into a target space in the neuroforamen dorsal to the DRG and below the vertebral lamina. A paddle body of the paddle lead may include a living hinge and/or a contoured profile to further facilitate implantation in the target space. For suture assisted deployment as well as to resist migration of the paddle lead once deployed, the paddle lead may include a suture loop configuration. The paddle lead further includes an electrode array having electrode contacts arranged in a two dimensional configuration pattern to create an electrical field optimized for stimulation of the DRG.

20 Claims, 20 Drawing Sheets

Related U.S. Application Data continuation of application No. 16/684,717, filed on Nov. 15, 2019, now Pat. No. 11,464,965, which is a division of application No. 15/333,999, filed on Oct. 25, 2016, now abandoned.

(56) References Cited

U.S. PATENT DOCUMENTS

| | | | |
|---|---|---|---|
| 9,162,055 | B2 | 10/2015 | Pianca et al. |
| 9,205,261 | B2 | 12/2015 | Kim et al. |
| 9,956,000 | B2 | 5/2018 | Gardanier et al. |
| 2006/0161235 | A1 | 7/2006 | King |
| 2008/0046049 | A1 | 2/2008 | Skubitz et al. |
| 2008/0140152 | A1 | 6/2008 | Imran et al. |
| 2008/0215106 | A1 | 9/2008 | Lee et al. |
| 2010/0063568 | A1 | 3/2010 | Staunton et al. |
| 2011/0130805 | A1 | 6/2011 | Goel |
| 2011/0172751 | A1 | 7/2011 | Lee |
| 2012/0029528 | A1 | 2/2012 | Macdonald et al. |
| 2012/0209283 | A1 | 8/2012 | Zhu |
| 2012/0215218 | A1 | 8/2012 | Lipani |
| 2012/0316610 | A1 | 12/2012 | Pianca et al. |
| 2013/0238076 | A1 | 9/2013 | Feler |
| 2013/0282091 | A1 | 10/2013 | Leven |
| 2013/0289685 | A1 | 10/2013 | Browne et al. |
| 2013/0317583 | A1 | 11/2013 | Pianca |
| 2014/0031837 | A1 | 1/2014 | Perryman et al. |
| 2014/0100639 | A1 | 4/2014 | Lee et al. |
| 2014/0128954 | A1 | 5/2014 | Schüttler et al. |
| 2014/0343564 | A1 | 11/2014 | Feler et al. |
| 2015/0174395 | A1 | 6/2015 | Goel |
| 2016/0067477 | A1 | 3/2016 | Dubuclet |
| 2016/0166828 | A1 | 6/2016 | Yu |
| 2016/0310725 | A1 | 10/2016 | De La Rama et al. |
| 2017/0173335 | A1 | 6/2017 | Min et al. |

OTHER PUBLICATIONS

Australian Examination Report No. 1, AU2020204048, dated Feb. 22, 2022.

Canadian Examination Report, CA 3041793, Aug. 10, 2023, 3 pgs.

European Examination Report, EP 17864179.1, dated Dec. 6, 2022, 3 pgs.

European Examination Report, EP17864179.1, dated Feb. 14, 2022.

Extended European Search Report, EP17864179.1, dated Nov. 13, 2019.

International Search Report and Written Opinion, PCT/US2017/038772, dated Oct. 13, 2017.

Japanese Decision of Final Rejection, JP2019-543161, dated Mar. 15, 2022 (English).

Japanese Office Action, JP 2019-543161, Nov. 8, 2022, 4 pgs.

Japanese Office Action, JP 2019-543161, dated Feb. 7, 2023, 5 pgs.

Japanese Office Action, JP 2022-114160, dated Oct. 31, 2023, 4 pgs.

Japanese Office Action, JP2019-543161, dated May 25, 2021 (English).

Apr. 15, 2025—(JP) Office Action—App 2024-010919, 5 Pages.

Examination Report No. 1 for Application No. 2024203911 dated Jul. 21, 2025 (4 pages).

DORSAL ROOT GANGLIA SURGICAL LEADS

CROSS REFERENCE TO RELATED APPLICATIONS

The present application is a continuation application of U.S. application Ser. No. 17/893,358 filed Aug. 23, 2022, now U.S. Pat. No. 12,121,717 and titled "DORSAL ROOT GANGLIA SURGICAL LEADS," which is a continuation application of U.S. application Ser. No. 16/684,717 filed Nov. 15, 2019, now U.S. Pat. No. 11,464,965, and titled "DORSAL ROOT GANGLIA SURGICAL LEADS," which is a divisional application of U.S. application Ser. No. 15/333,999 filed Oct. 25, 2016, and titled "DORSAL ROOT GANGLIA SURGICAL LEADS," now abandoned. All the above-referenced applications are incorporated herein by reference in their entirety.

TECHNICAL FIELD

Aspects of the present disclosure relate to leads surgically implantable in a patient for electrical stimulation of nerve or tissue and more particularly to leads providing controlled stimulation of a spinal and/or paraspinal nerve root ganglion, such as a dorsal root ganglion.

BACKGROUND

Medical conditions may be treated through the application of electrical stimulation. For example, Spinal Cord Stimulation (SCS) involves driving an electrical current into particular regions of the spinal cord to induce paresthesia, which is a subjective sensation of numbness or tingling in a region of the body associated with the stimulated spinal cord region. Paresthesia masks the transmission of chronic pain sensations from the afflicted regions of the body to the brain, thereby providing pain relief to the patient. Typically, an SCS system delivers electrical current through electrodes implanted along the dura layer surrounding the spinal cord. The electrodes may be carried, for example, by a paddle lead, which has a paddle-like configuration with the electrodes arranged in one or more independent columns on a relatively large surface area, or a percutaneous lead, which includes the electrodes arranged around a tube. Paddle leads are generally delivered into the affected spinal tissue through a laminectomy, involving the removal of laminar vertebral tissue to allow access to the dura layer and positioning of the paddle lead. Conventional delivery of paddle leads thus generally requires large incisions and substantial removal of lamina, resulting in trauma to the patient and longer procedure time. On the other hand, however, paddle leads may resist migration once implanted, provide enhanced stimulation, and utilize less energy, among other advantages. Further, paddle leads may be advantageous as revision leads because scarring caused by a primary lead may inhibit placement of a percutaneous revision lead. As such, there is a need for paddle leads deployable from a minimally invasive surgical approach. It is with these observations in mind, among others, that various aspects of the present disclosure were conceived and developed.

SUMMARY

Implementations described and claimed herein address the foregoing problems, among others, by providing dorsal root ganglia stimulation leads and methods of implanting the same. In one implementation, a paddle body extends between a proximal end and a distal end. A lead body extends from the proximal end forming a paddle lead. An electrode array is disposed on at least one surface of the paddle body. The electrode array has one or more electrode contacts arranged in an electrode array configuration. A tapered distal tip is formed by the paddle body tapering in width toward the distal end. The tapered distal tip is shaped for surgical placement of the paddle body below vertebral lamina dorsal to the dorsal root ganglion following a medial laminectomy and ligament removal. The surgical placement orients the electrode array for the electrical stimulation of the dorsal root ganglion.

In another implementation, a paddle body extends between a proximal end and a distal end, and a lead body extends from the proximal end. An electrode array is disposed on at least one surface of the paddle body. The electrode array has one or more electrode contacts arranged in a two-dimensional electrode array configuration forming an asymmetrical paddle lead with the electrical stimulation focused in a single direction within a target area of the dorsal root ganglion. A living hinge is formed by the paddle body extending from a first side to a first hinge and from a second side to a second hinge. The first and second hinges each form a joint configured to bend the paddle body along a contour to cradle the dorsal root ganglion.

In still another implementation, a paddle body extends between a proximal end and a distal end. A lead body extends from the proximal end forming a paddle lead. An electrode array is disposed on at least one surface of the paddle body. The electrode array has one or more electrode contacts arranged in a two-dimensional electrode array configuration. A suture loop configuration has one or more suture loops for suture guided deployment of the paddle lead.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the present disclosure involve paddle leads for dorsal root ganglia (DRG) stimulation and methods of implanting the same. Generally, a paddle lead is implanted in a target area of a patient through access to the foraminal space above the DRG using a minimally invasive approach. In one aspect, the paddle lead has a small profile facilitating deployment into the neuroforamen dorsal to the DRG below the vertebral lamina. The small profile may include, for example, a thin cross-section facilitating placement below the lamina and resisting displacement of the DRG during implantation. The paddle lead profile would thus be adapted for deployment in a DRG target area, such as lumbar or thoracic neuroforamen caudal to the pedicles. A paddle body of the paddle lead may be further adapted for implantation in the target space. For example, the paddle body may include a living hinge and/or have a contoured profile for flexible placement and functionality within the target space. Wires or formable plates may be used to maintain the shape of the paddle body and/or other portions of the paddle lead. To further facilitate placement as well as resist migration once deployed, the paddle lead may include a suture loop configuration having one or more suture holes for securing the paddle lead to bone anchors, tissue, and/or the like within the target space.

In one aspect, the paddle lead includes an electrode array with a directionality to focus the stimulation. The directionality, for example, may focus the stimulation in one direction to overcome stimulation loss caused by scar tissue present in the target area. The directionality may further reduce power consumption by the paddle lead. The electrode array includes one or more electrode contacts arranged to maximize programming potential for DRG stimulation. The electrode array may have a two-dimensional (2D) configuration pattern, increasing subdermatomal specificity. The asymmetrical design of the paddle lead improves stability, for example, in the left or right neuroforamen.

Figure 1:
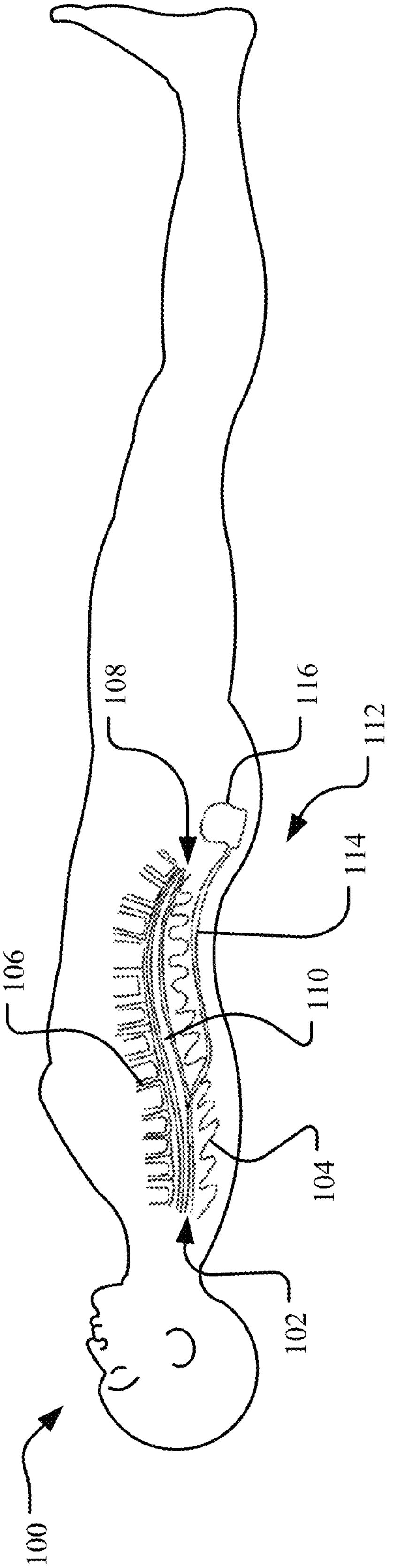
FIG. 1 shows a patient with an example lead implanted for Spinal Cord Stimulation (SCS).

To begin a detailed description of treatment to a patient 100 for a medical condition, such as chronic pain, through the application of electrical stimulation to a target area, reference is made to FIG. 1. In the vertebrate spinal column of the patient 100, the epidural space 102 is positioned at the outermost part of the spinal canal formed by vertebrae 106, which have spinous process 104 projecting therefrom and providing a point of attachment for muscles and ligaments of the patient 100. Ligamentum flavum 108 connect the laminae of adjacent vertebrae 106. The lamina covers the spinal canal, which encloses and protects the spinal cord 110. In one implementation, an implantable DRG stimulation system 112 includes a paddle lead 114 positioned at a target area in the epidural space 102 to drive an electrical current from a power source 116 into particular regions of the spinal cord 110 of the patient 100, such as the DRG, to induce paresthesia. The power source 116 may be an implantable pulse generator (IPG) or an external pulse generator (EPG).

In one implementation, the paddle lead 114 has a lead body extending proximally from a paddle body to the power source 116. The power source 116 delivers power to an electrode array disposed on or along the paddle body, which is implanted in the target area of the patient 100. The electrode array of the paddle lead 114 includes an electrode configuration pattern, such as a 2D (i.e., nonlinear) configuration pattern, to deliver electrical stimulation to a DRG in the target area of the patient 100. As described herein, the paddle lead 114 may provide a directionality of the electrical stimulation. In one implementation, the directionality of the electrode array of the paddle lead 114 focuses the stimulation in one direction to overcome stimulation loss caused by scar tissue present in the target area of the patient 100. Such scar tissue may be present in the target area, for example, due to the previous implantation of a primary lead. The directionality may further reduce power output by the power source 116 and consumed by the paddle lead 114.

The paddle body of the paddle lead 114 may further be sized and shaped to facilitate navigating the spinal anatomy of the patient 100 during deployment of the paddle lead 114 and once implanted, to provide a flexibility of the paddle lead 114 during electrical stimulation. For a non-limiting example of a percutaneous or other minimally invasive deployment of the paddle lead 114 for SCS treatment, reference is made to FIGS. 2-7.

Figure 2:
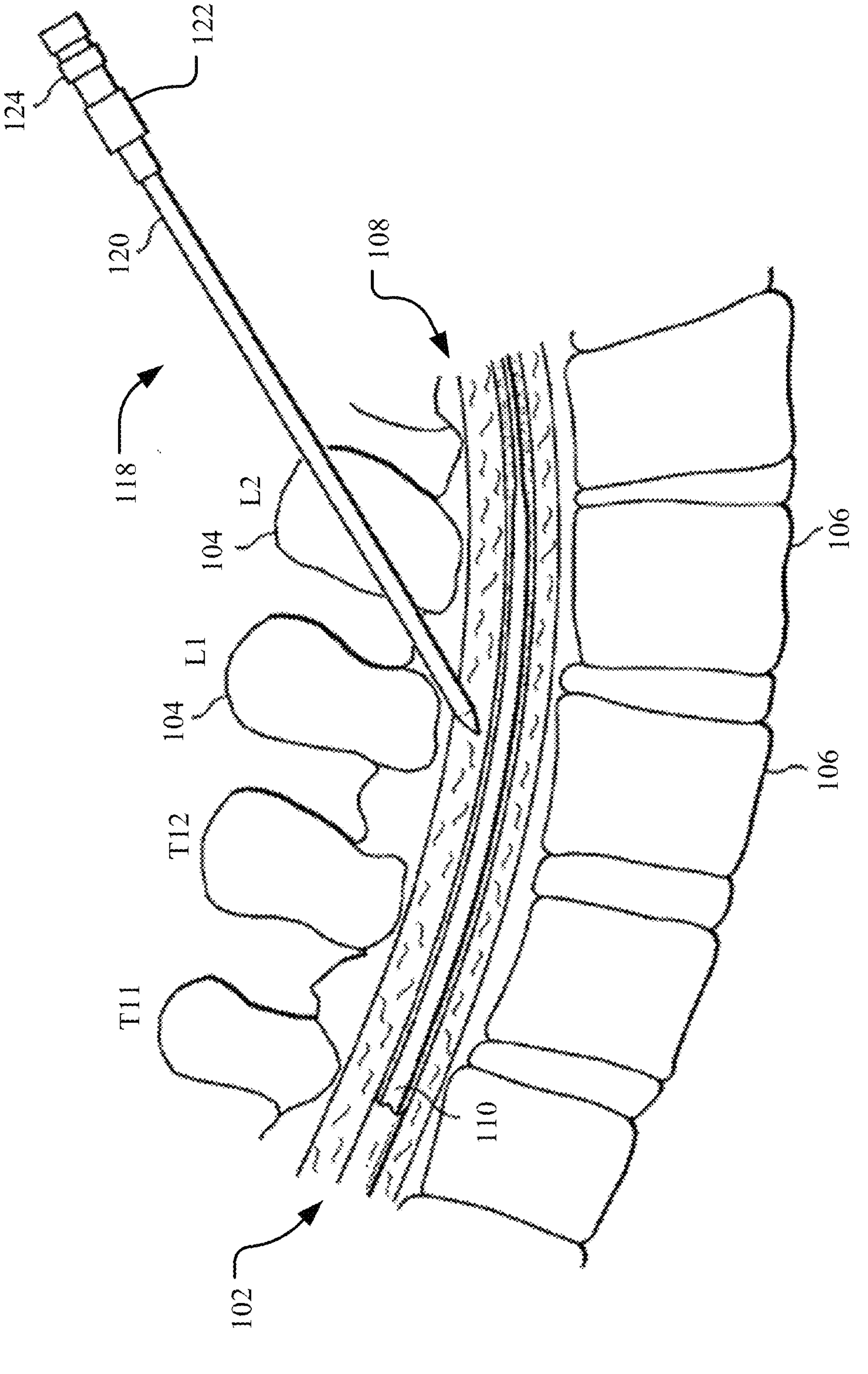
FIG. 2 shows an example deployment system and method for implanting a paddle lead for SCS, the deployment system shown with a needle inserted into epidural space of the patient.

Turning first to FIG. 2, in one implementation, a target area in the epidural space 102 of the patient 100 is chosen for positioning the paddle body of the paddle lead 114 to deliver SCS treatment to the target area, such as a DRG. The target area may be selected, for example, using fluoroscopy. Referring to FIG. 2, in one implementation, a deployment system 118 includes a needle 120, which is inserted through a small incision, for example, between the spinous processes 104 of two vertebrae 106. The needle 120 is advanced through subcutaneous tissue and the ligamentum flavum 108 of the spine into the epidural space 102 along the spinal cord 110. In one implementation, the needle 120 is inserted at an angle. Following entry of the needle 120 into the epidural space 102, an inner portion 124 (e.g., a stylet) is removed from a proximal end 122 of the needle 120.

Figure 3:
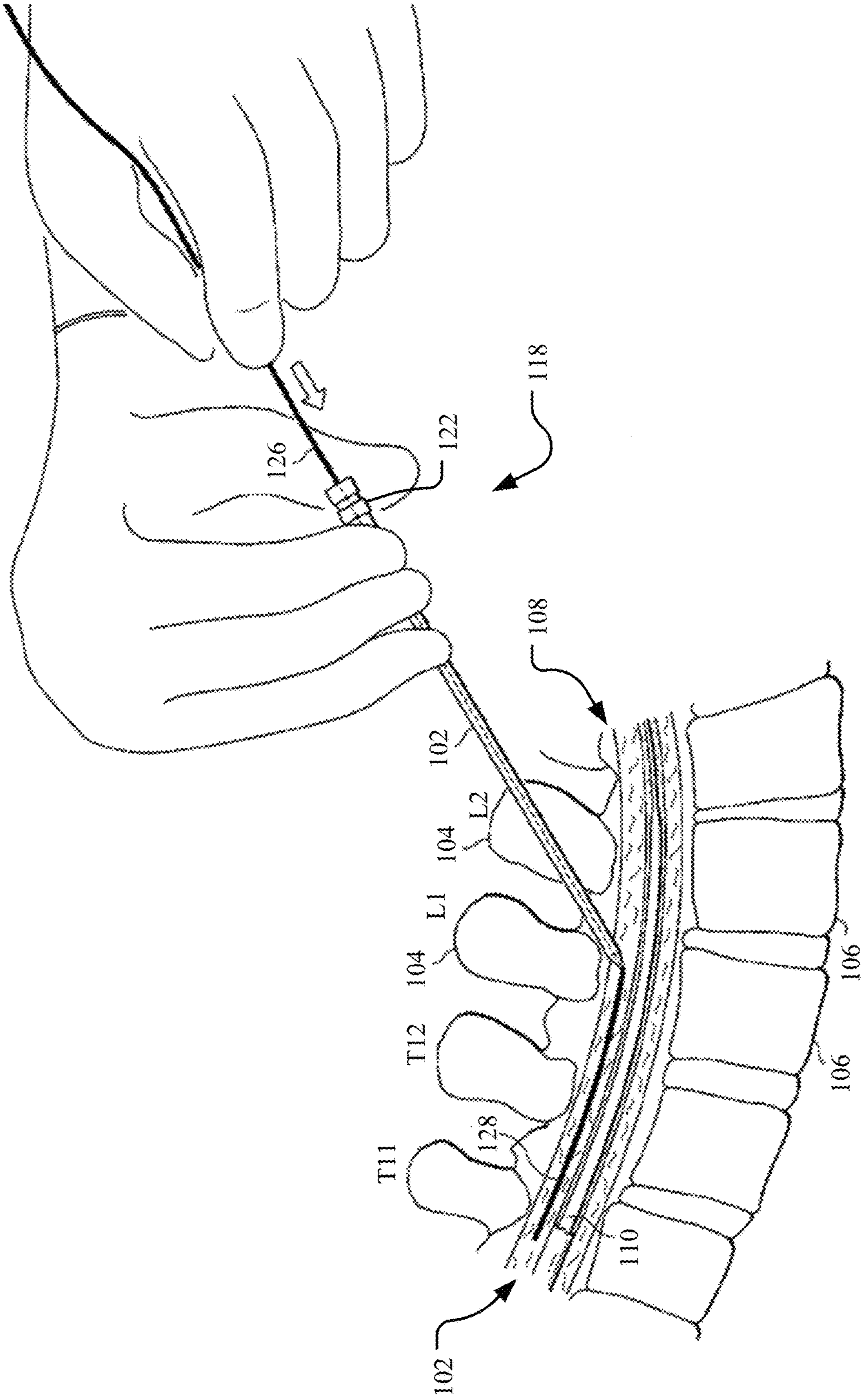
FIG. 3 illustrates the deployment system of FIG. 2 with a guide wire inserted through the needle into the epidural space of the patient.

Referring to FIG. 3, in one implementation, after removing the inner portion 124 from the needle 120, a guide wire 126 is inserted through the needle 120 into the epidural space 102. Fluoroscopy may be used to verify a position of a distal end 128 of the guide wire 126 in the target area of the epidural space 102. Once the distal end 128 of the guide wire 126 is positioned, the needle 120 is removed.

Figure 4:
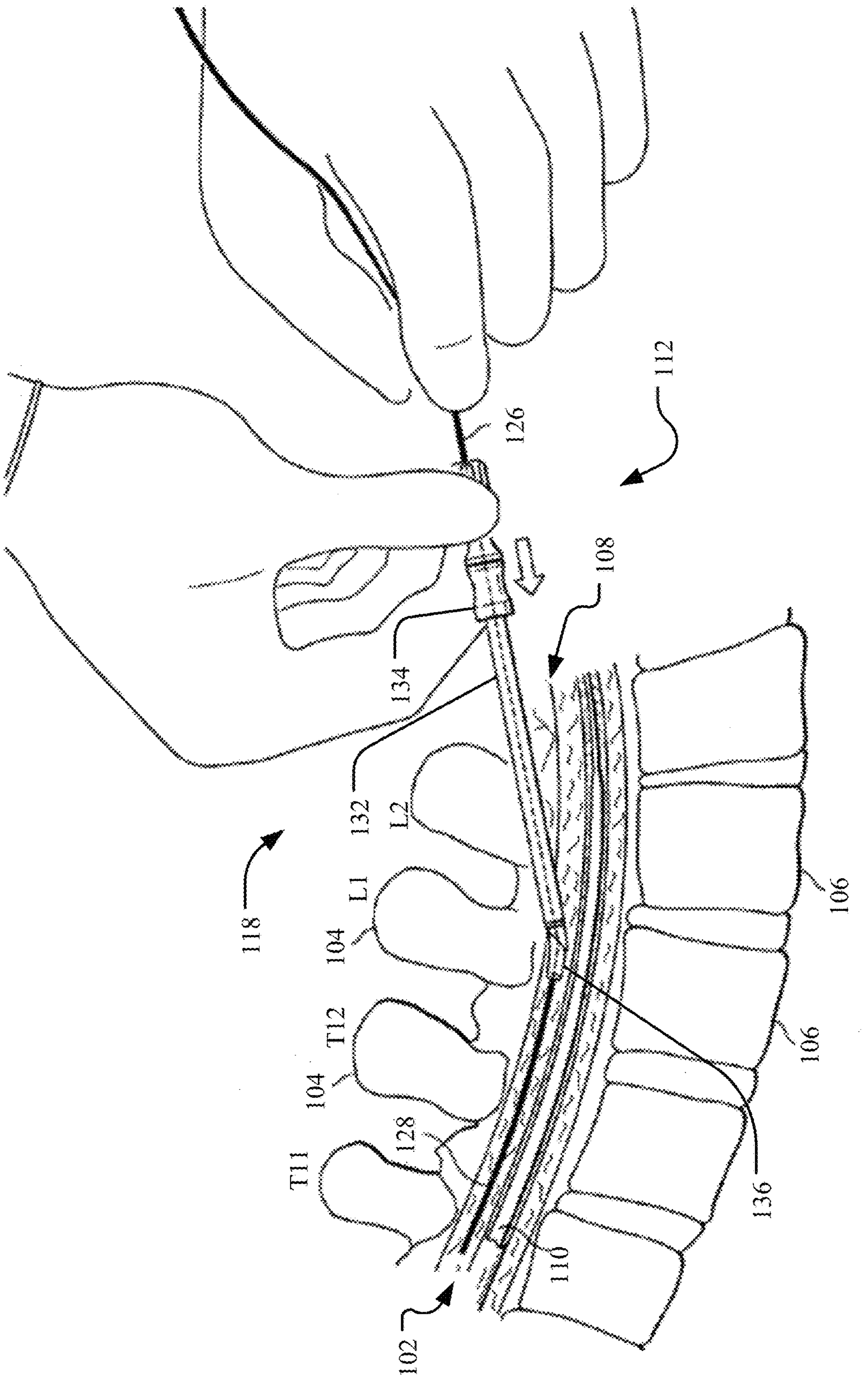
FIG. 4 illustrates the deployment system of FIG. 3 with a delivery tool inserted over the guide wire into the epidural space of the patient.

As shown in FIG. 4, a delivery tool 130 having a sheath 132 extending from a hub 134 is deployed over the guide wire 126 into the epidural space 102. In one implementation, a distal tip of the sheath 132 has a spatula shape including a narrow neck extending distally into a broad rounded apex. The distal tip of the sheath 132 may be approximately ten to thirty percent larger than a size of the paddle body of the paddle lead 114. The sheath 132 may be contourable, flexible, rigid, and/or have portions with one or more combinations thereof to facilitate navigation of the anatomy of the patient 100.

Figure 5:
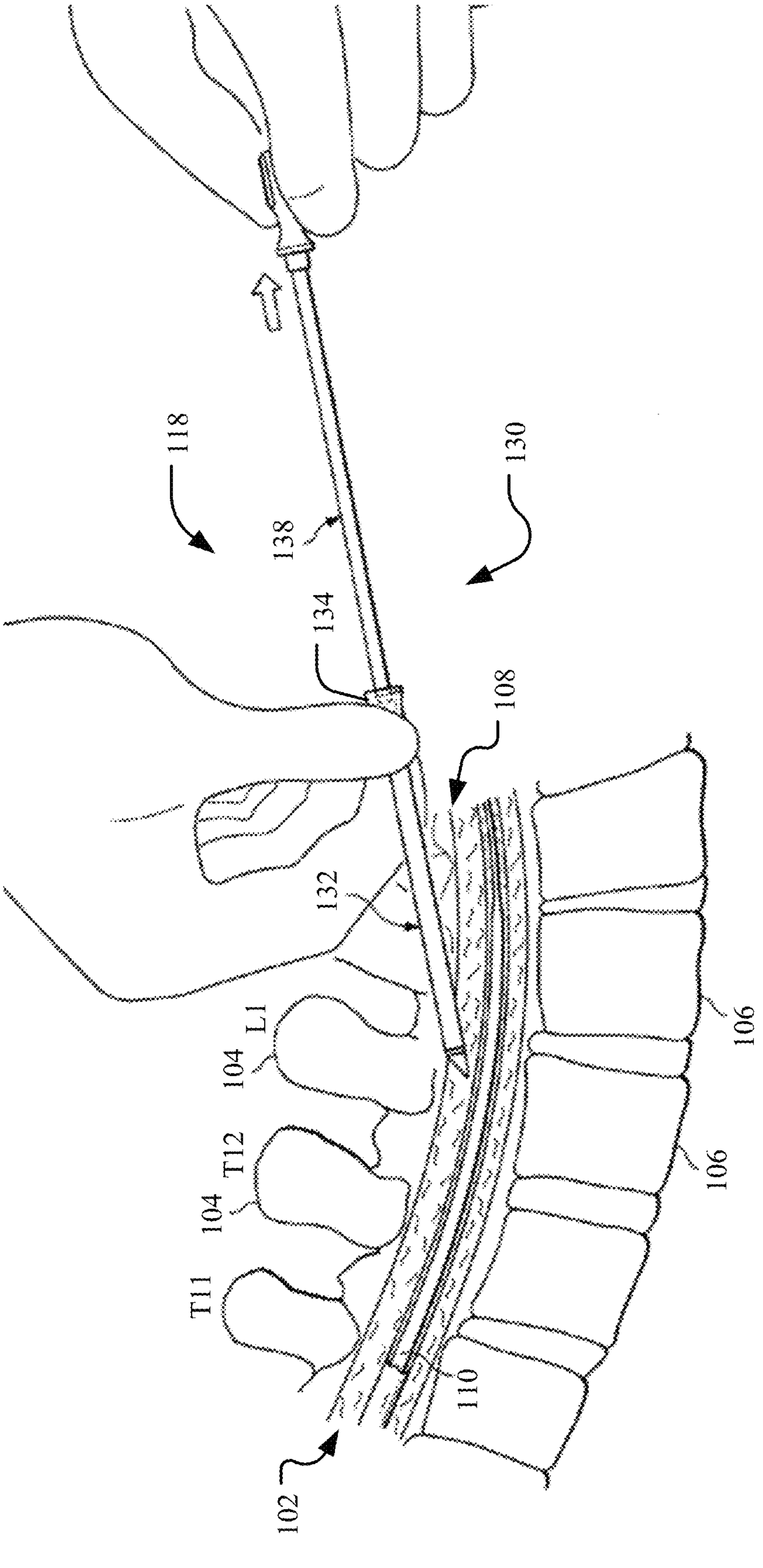
FIG. 5 shows the deployment system of FIG. 4 with an inner penetrator being removed from a sheath of the delivery tool.

The delivery tool 130 may be inserted at an angle. In one implementation, as can be understood from FIGS. 4-5, a dilator 136 extends through a distal tip of the sheath 132 from an inner penetrator 138, permitting the delivery tool 130 to pass easily over the guide wire 126 without creating a false passage in an undesirable location of the anatomy of the patient 100. The dilator 136 may further provide indication to the surgeon of contact with the ligamentum flavum 108. Once the delivery tool 130 penetrates the ligamentum flavum 108, the guide wire 126 is removed, leaving the sheath 132 positioned in the epidural space 102. As shown in FIG. 5, in one implementation, the inner penetrator 138 is also removed.

Figure 6:
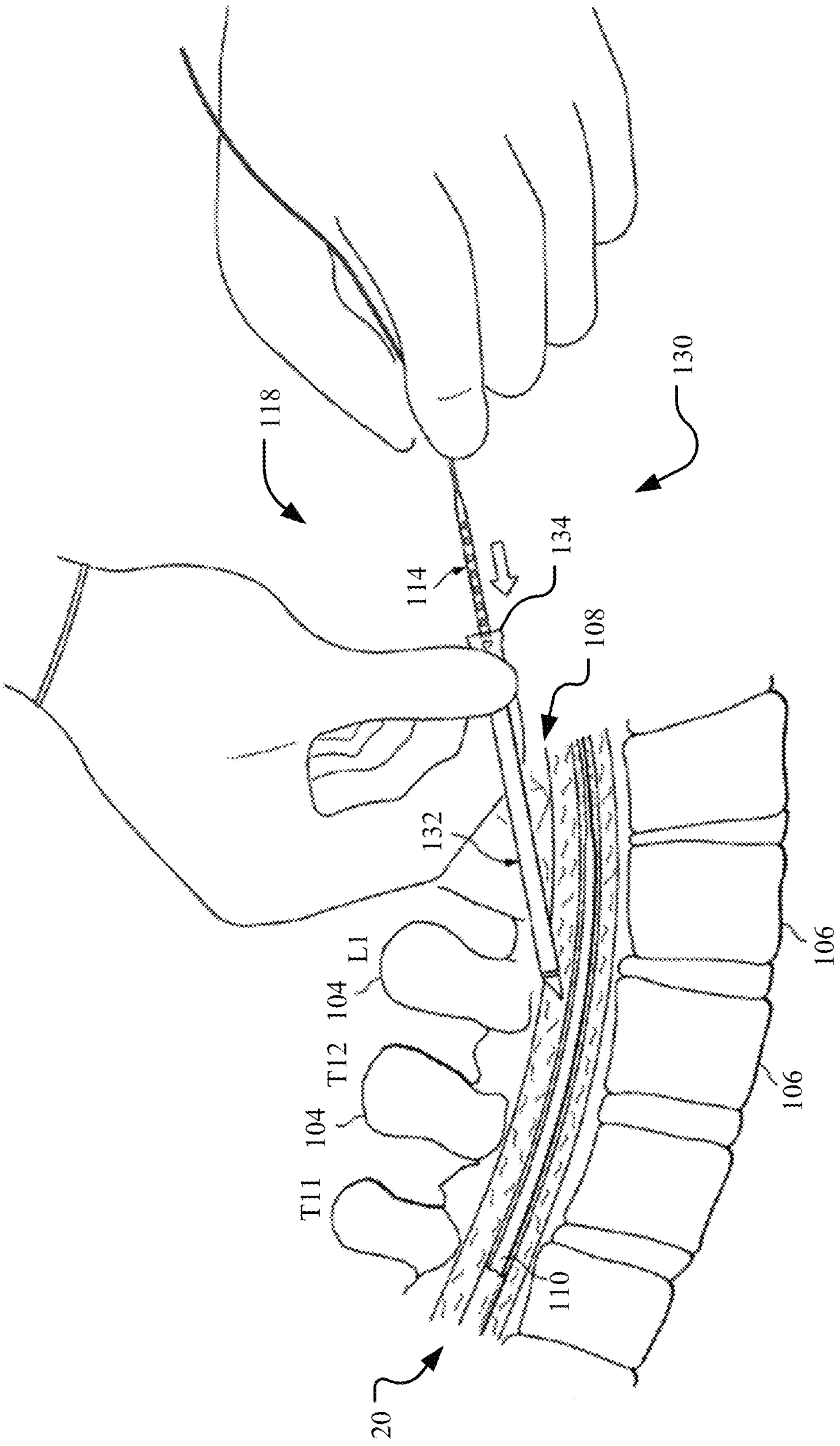
FIG. 6 illustrates the deployment system of FIG. 5 with the paddle lead being inserted through the sheath of the delivery tool into the epidural space of the patient.
Figure 7:
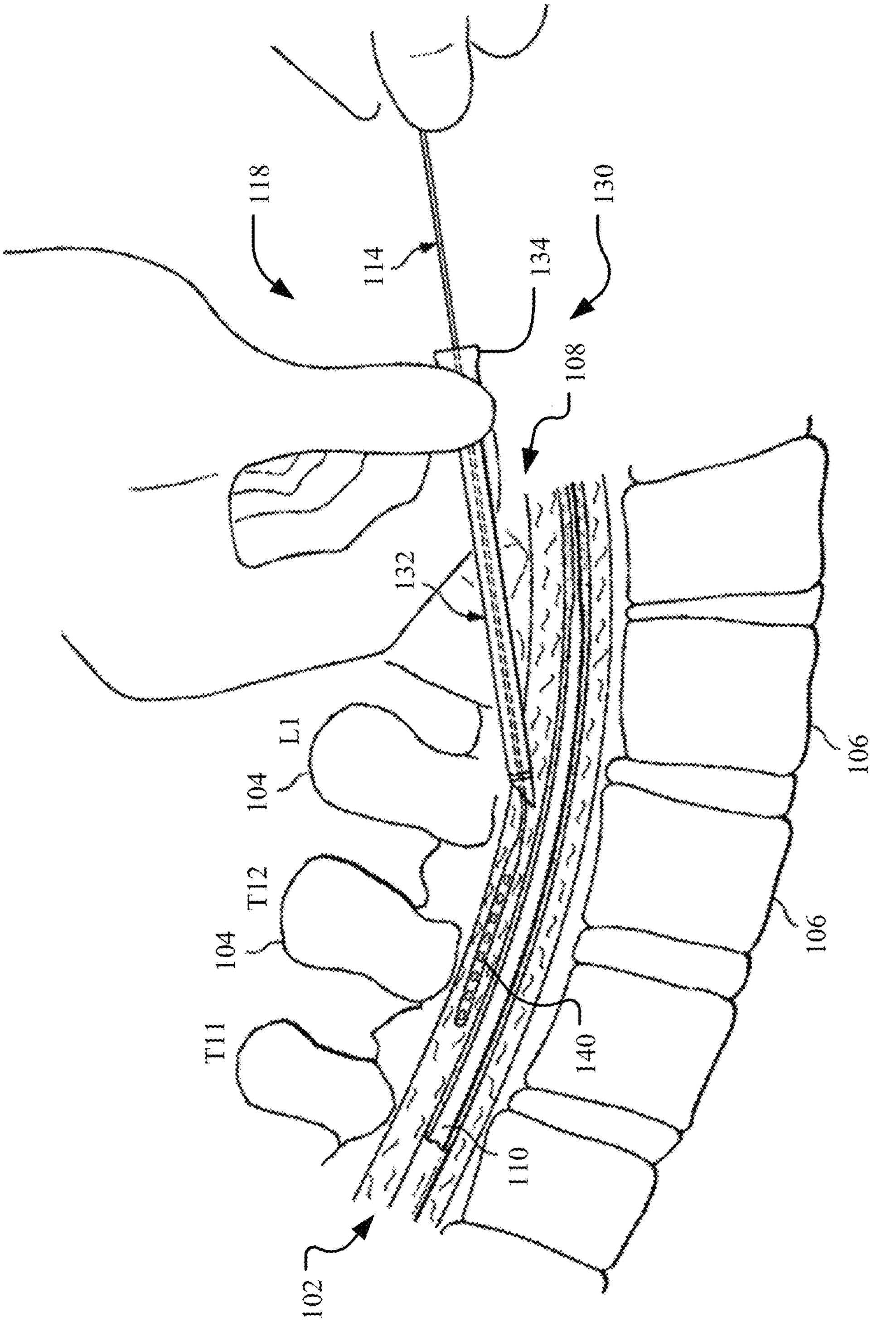
FIG. 7 illustrates the paddle lead implanted and the delivery tool of the paddle lead deployment system of FIG. 6 being removed from the epidural space of the patient.

Referring to FIGS. 6 and 7, the paddle lead 114 is inserted through a lumen of the sheath 132 into the target area of the patient 100 in the epidural space 102. The sheath 132 is then removed, leaving the paddle lead 114 in the epidural space 102 to deliver electrical stimulation to the target area using power drawn from the power source 116 and delivered using an electrode array 140. In one implementation, the paddle lead 114 is secured in the target area by suturing it to a spinous process (e.g., one of the spinous processes 104) using a suture loop configuration of the paddle lead 114. Stated differently, the deployment of the paddle lead 114 may be suture guided.

Figure 8:
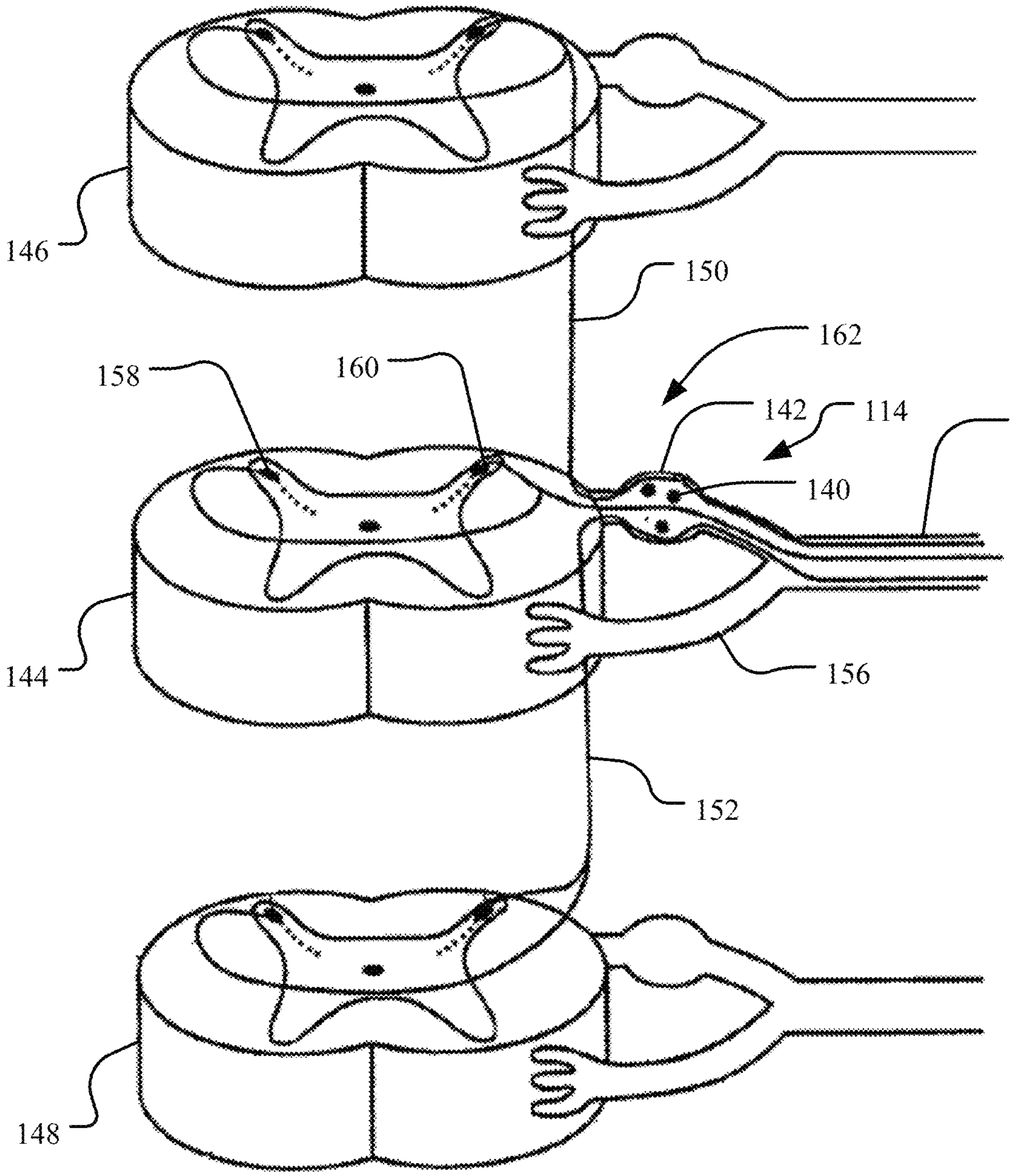
FIG. 8 illustrates the paddle lead implanted into neuroforamen dorsal to a dorsal root ganglion (DRG) of a spinal level of the patient, with the foraminal space above the DRG accessed from a minimally invasive surgical approach for implantation.

Turning to FIG. 8, in one implementation, the paddle lead 114 is implanted in the target area with the electrode array 140 and positioned to deliver electric stimulation to a DRG 142. The paddle lead 114 may be positioned upon the dura layer of the spinal cord 110, such that the electrode array 140 stimulates a wide portion of the spinal cord 110 and the associated nerve tissue. The spinal cord 110 is a continuous body with a plurality of spinal levels. For clarity, three spinal levels 144, 146, and 148 are shown in FIG. 8. Each of the spinal levels 144-148 are subsections of the spinal cord 110 depicted in FIG. 8 with the portion where the dorsal root and the ventral root join the spinal cord 110. The peripheral nerve 154 divides into the DRG 142 and the ventral root nerve 156, each of which feed into the spinal cord 110.

Dorsal horns 158 and 160 connect the spinal levels. For example, a second spinal level 144 is connected to a first spinal level 146 via an ascending pathway 150, and the second spinal level 144 is connected to a third spinal level 148 via a descending pathway 152. Application of electrical stimulation to the DRG 142 in the second spinal level 144 may be used to block signals progressing upstream from the second spinal level 144 to the ascending pathway 150. Modulation applied to portions of the second spinal level 144 may further be used to block the neuron pathways from the first spinal level 146 or third spinal level 148 from reaching the brain of the patient 100, thereby blocking intrasegment pain pathways.

In one implementation, the paddle lead 114 is implanted into neuroforamen dorsal to the DRG 142 of one of the spinal levels (e.g., the second spinal level 144) of the patient 100, with the foraminal space above the DRG 142 accessed from a minimally invasive surgical approach for implantation. A medial laminectomy is performed to remove lateral laminar and ligament to access the foraminal space. To assist dissection, a spacer 162 having a contourable body may be placed and the paddle lead 114 deployed into the lumbar or thoracic neuroforamen caudal to the pedicles. The paddle lead 114 is positioned in the target area over the DRG 142. In one implementation, the paddle lead 114 includes a suture loop configuration, permitting the paddle lead 114 to be pulled through the spinal anatomy of the patient 100 into the target area using one or more sutures. In addition to this suture assisted deployment, the paddle lead 114 may be secured over the DRG 142 in the target area using the suture loop configuration.

The paddle lead 114 has a thin, compact, low profile, shaped to facilitate minimally invasive surgical placement. In one implementation, a distal tip of the paddle lead 114 tapers permitting placement over the DRG 142. Alternatively or additionally, the paddle body of the paddle lead 114 may have a living hinge creating a contouring of the paddle body to hug or otherwise provide substantially continuous contact with the DRG 142. The paddle lead 114 may be made from a contourable material for pliable shaping of the paddle body. Further, the paddle lead 114 may include formable elements, such as wire(s) and/or coil(s) to enhance and maintain the contouring.

The electrode array 140 has one or more electrode contacts arranged in an electrode array configuration to create an electrical field optimized for stimulation of the DRG 142. In one implementation, the electrode array 140 includes a 2D configuration pattern, enhancing specificity and selectivity. For example, the electrode array configuration may include electrodes arranged in a four by two by two pattern, a six by three by three pattern, a two by two pattern, or the like. The electrode array 140 may be configured for high frequency and/or burst stimulation patterns.

FIGS. 9-24 depict various examples of the paddle lead 114 configured for delivery of electrical stimulation to the DRG 142. It will be appreciated by those of ordinary skill in the art that such depictions are exemplary only and not intended to be limiting.

Figure 9:
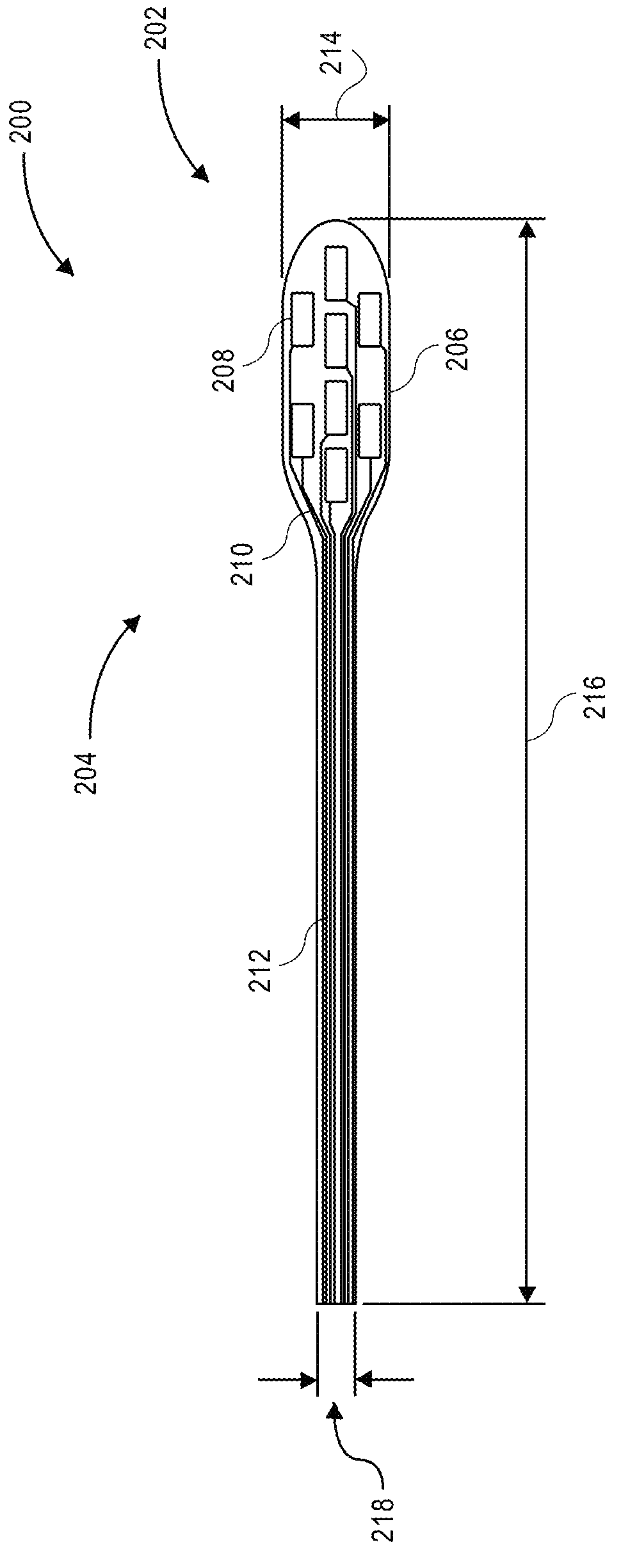
FIG. 9 depicts an example paddle lead for DRG stimulation.
Figures 10A, 10B, 10C, 10D:
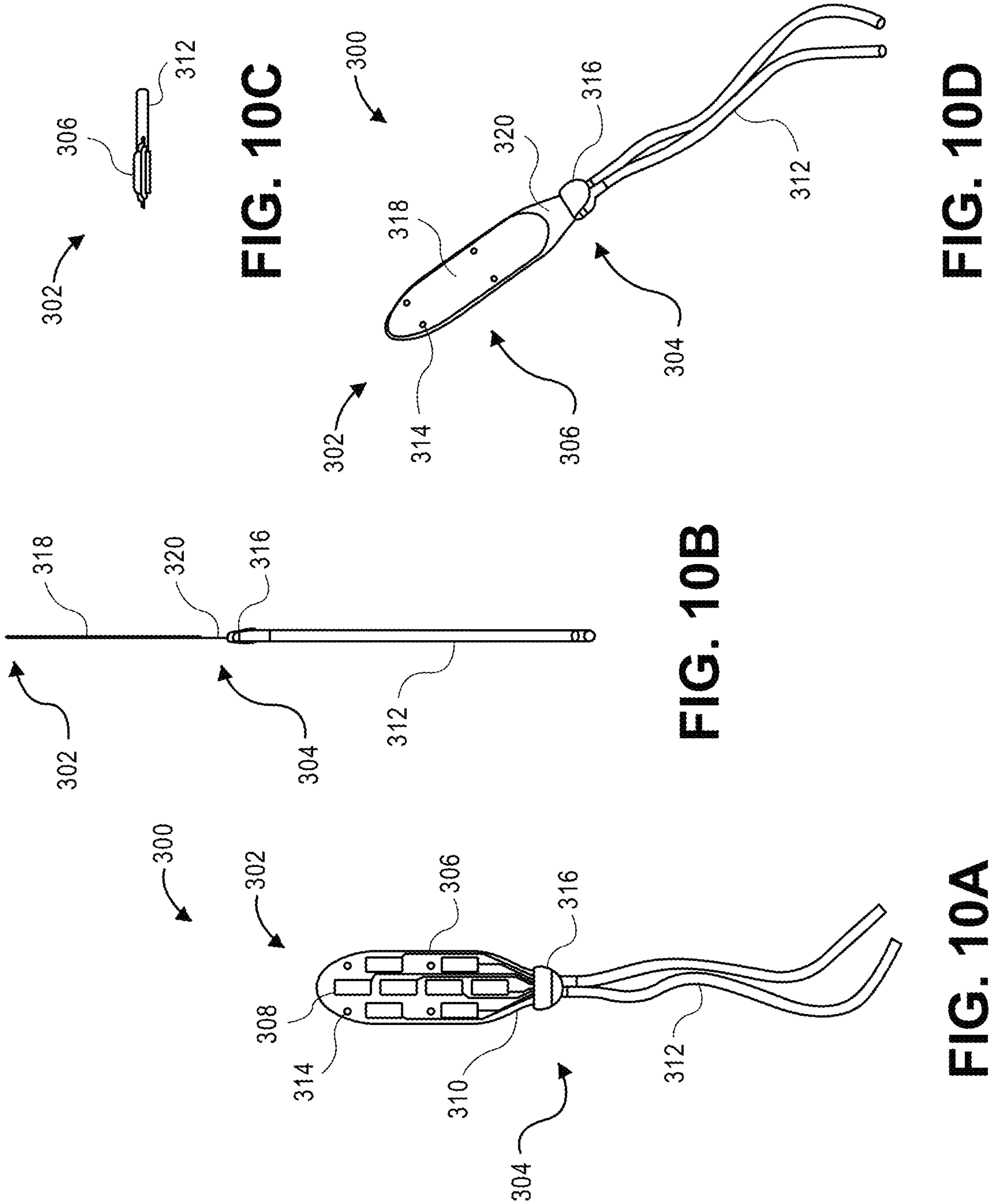
FIGS. 10A-10D show front, side, distal, and back perspective views, respectively, of another example paddle lead for DRG stimulation.

Turning first to FIG. 9, in one implementation, a paddle lead 200 for DRG stimulation includes a paddle body 206 extending between a distal end 202 and a proximal end 204. The paddle body 206 tapers distally at the distal end 202 to form a tapered distal tip. A lead body 212 extends from the proximal end 204 of the paddle body 206. An electrode array having a plurality of electrodes 208 arranged in a 2D configuration pattern are disposed on a surface of the paddle body 206. Power is supplied to the electrodes 208 via trace conductors 210, which electrically connect the electrodes 208 to the power source 116 directly or indirectly.

The paddle lead 200 has a thin, compact, low profile, as discussed herein. In one example implementation, the paddle lead 200 has a length 216 of approximately 2.865 inches; the paddle body 206 has a width 214 of approximately 0.275 inches; and the lead body 212 has a width 218 of approximately 0.100 inches. Other dimensions are contemplated.

FIGS. 10A-10D show front, side, distal, and back perspective views, respectively, of another example paddle lead 300 for DRG stimulation. In one implementation, the paddle lead 300 includes a paddle body 306 extending between a distal end 302 and a proximal end 304. The paddle body 306 tapers distally at the distal end 302 to form a tapered distal tip.

A lead body assembly 312 extends from the proximal end 304 of the paddle body 306. The lead body assembly 312 may have one or more elongated bodies that are fixed, contourable, flexible, and/or rigid. In one implementation, the lead body assembly 312 has one or more conductive wires or coils connected to trace conductors 310 via a lead connector 316, which may be made, for example, from molded silicone or other polymers. Each of the trace conductors 310 electrically connects a corresponding electrode contact 308 in an electrode array to supply electrical energy for stimulation of the DRG 142.

The electrode array includes the electrode contacts 308 arranged in a 2D configuration pattern on a surface of the paddle body 306, such that the paddle lead 300 is asymmetrical. The electrode contacts 308 may have varying sizes configured to optimize stimulation of the DRG 142. For example, the electrode contacts 308 may be approximately nine microns thick. In one implementation, the paddle body 306 includes a conformable plating 318 deposited on a base 320 opposite a surface on which the electrode contacts 308 and the trace conductors 310 are disposed. The conformable plating 318 may be used to achieve and maintain a profile shape of the paddle body 306. The base 320 may be made from a variety of biocompatible materials, including, but not limited to, Kapton or other polyimides. Again, the paddle lead 300 has a thin, compact, low profile, as shown in FIGS. 10A-10D. In one example, the conformable plate 318 has a thickness of approximately twenty-five microns and the base 320 has a thickness of approximately fifteen microns. A width of the base 318 may taper proximally from the conformable plate 318 into the lead connector 316.

For suture assisted deployment of the paddle lead 300, in one implementation, a suture loop configuration has one or more suture holes 314 defined in or disposed along the paddle body 306, the lead connector 316, and/or the lead body assembly 312. For example, as shown in FIGS. 10A-10D, the suture holes 314 may be defined in the paddle body 306 relative to the electrode contacts 308 with a first set disposed near the distal tip of the paddle body 306 and a second set disposed near a middle of the paddle body 306 so as not to interfere with the electrical pathways of the trace conductors 310 or the electrodes 308. The paddle lead 300 may be secured in the target area using one or more sutures extending through at least a portion of the suture loop configuration.

Figures 11A, 11B, 11C:
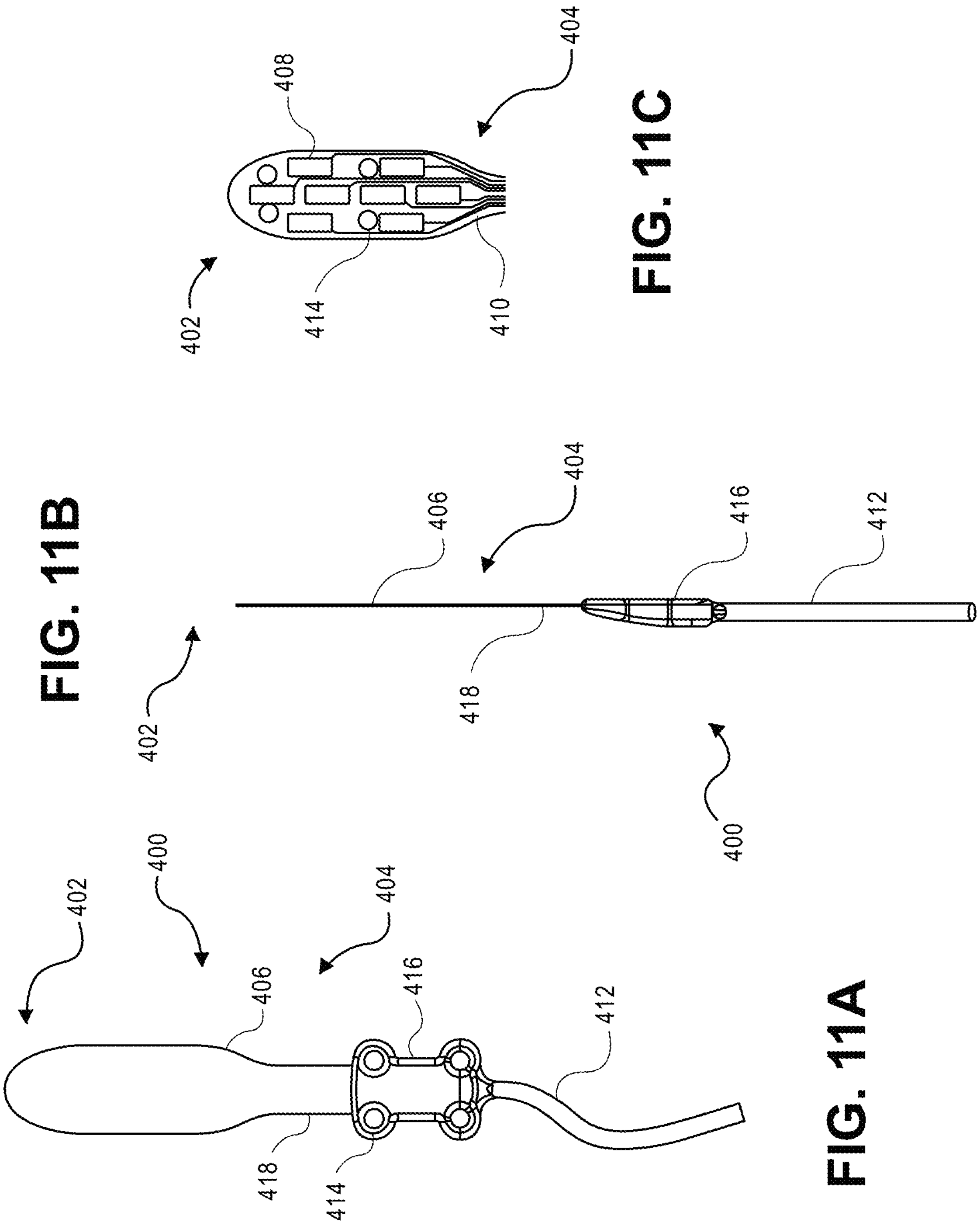
FIGS. 11A-11C are back, side, and front views, respectively of another example paddle lead for DRG stimulation.
Figure 12A:
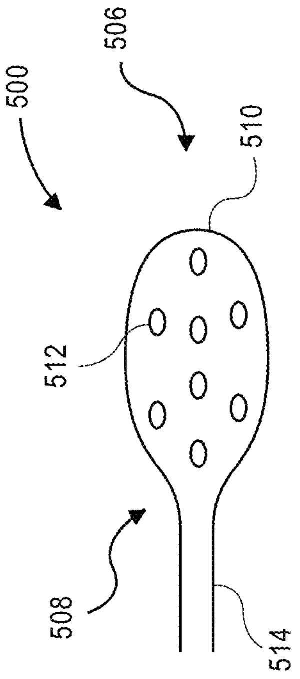
FIGS. 12A-12C show various example electrode array configurations for a paddle lead for DRG stimulation.
Figure 12B:
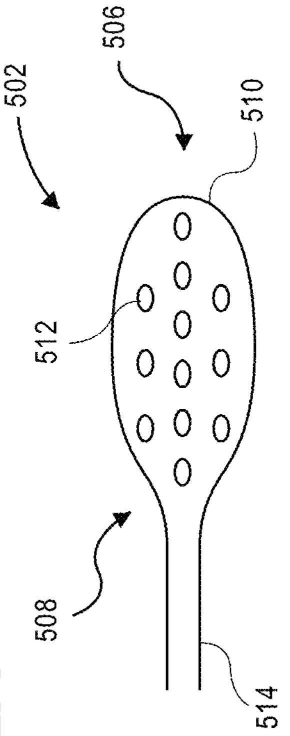
Figure 12C:
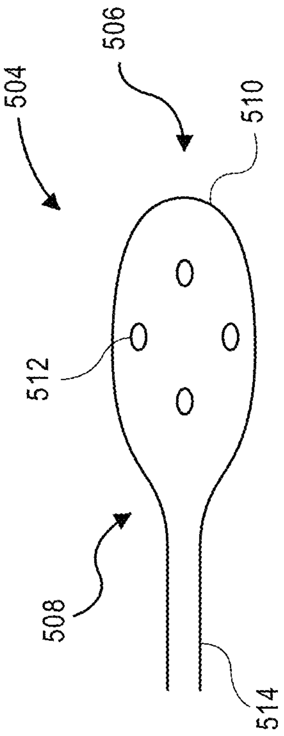
Figure 13A:
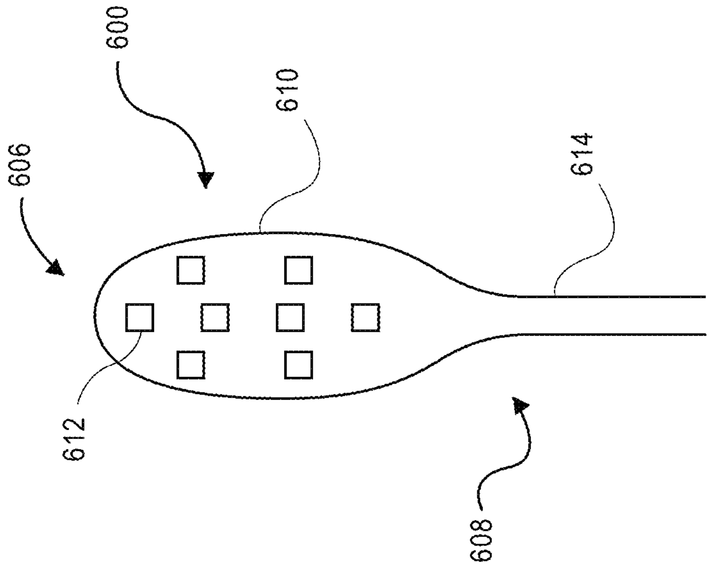
FIGS. 13A-13C illustrate example paddle leads for DRG stimulation with varying dimensions and electrode array configurations.
Figure 13B:
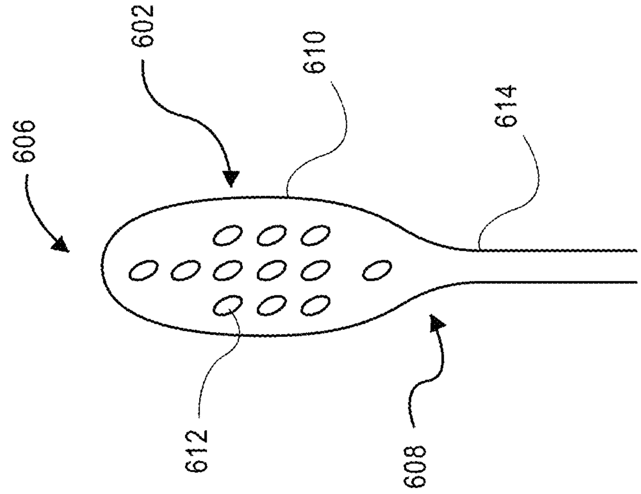
Figure 13C:
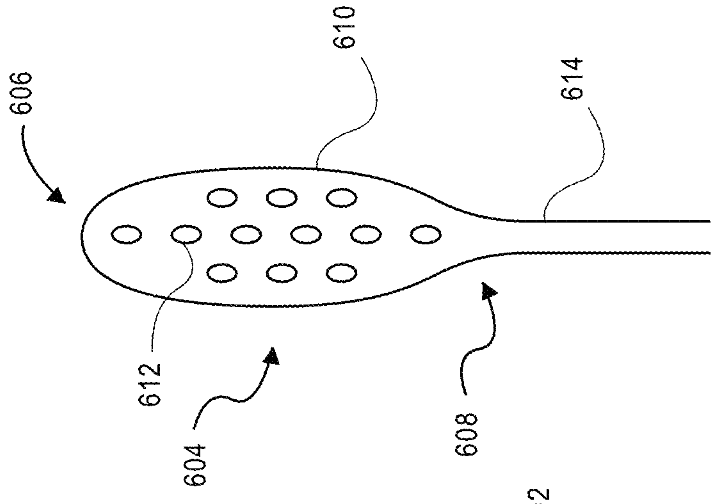
Figures 14A, 14B, 14C, 14D, 14E:
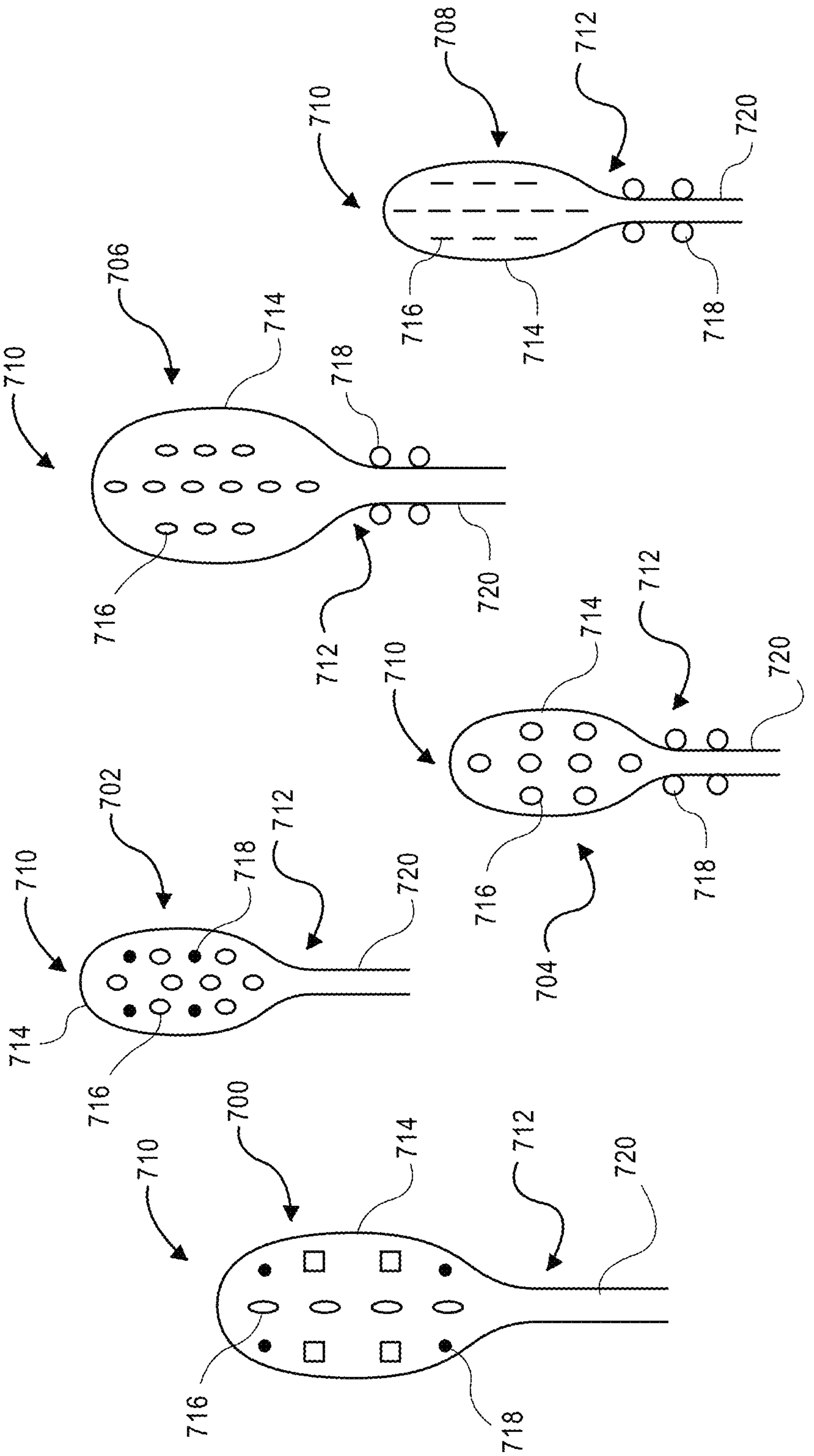
FIGS. 14A-14E show various example paddle leads for DRG stimulation with a suture loop configuration.

FIGS. 11A-11C are back, side, and front views, respectively, of another example paddle lead 400 for DRG stimulation. In one implementation, the paddle lead 400 includes a paddle body 406 extending between a distal end 402 and a proximal end 404. The paddle body 406 tapers distally at the distal end 402 to form a tapered distal tip. In one implementation, the paddle body 406 tapers proximally into a neck 418. The neck 418 may be elongated, for example, having a length of approximately 0.15 inches.

A lead body 412 extends from the neck 418. In one implementation, the lead body 412 has one or more conductive wires or coils connected to trace conductors 410 via a lead connector 416, which may be made, for example, from molded silicone or other polymers. Each of the trace conductors 410 electrically connects a corresponding electrode contact 408 in an electrode array to supply electrical energy for stimulation of the DRG 142.

The electrode array includes the electrode contacts 408 arranged in a 2D configuration pattern on a surface of the paddle body 406, such that the paddle lead 400 is asymmetrical. Again, the paddle lead 400 has a thin, compact, low profile, as shown in FIGS. 11A-11C. A thickness of the lead body 412 is greater than a thickness of the paddle body 406, which may be the same thickness as the neck 418. In one example, the lead body 412 has a diameter of approximately 0.055 inches.

For suture assisted deployment of the paddle lead 400, in one implementation, a suture loop configuration has one or more suture holes 414 defined in or disposed along the paddle body 406, the neck 418, the lead connector 416, and/or the lead body 412. For example, as shown in FIGS. 11A-11C, the suture holes 414 may be defined in the paddle body 406 relative to the electrode contacts 408 with a first set disposed near the distal tip of the paddle body 406 and a second set disposed near a middle of the paddle body 406 so as not to interfere with the electrical pathways of the trace conductors 410 or the electrodes 408. The suture holes 414 may further be defined in the lead connector 416 with a first set disposed at a distal end of the lead connector 416 near the neck 418 and a second set disposed at a proximal end of the lead connector 416 near the lead body 412. The paddle lead 400 may be secured in the target area using one or more sutures extending through at least a portion of the suture loop configuration.

As described herein, the paddle lead 114 includes an electrode array 140 for focused stimulation of the DRG 142. For examples of various non-limiting configurations 500-504 of the electrode array 140, reference is made to FIGS. 12A-12C. In one implementation, the paddle lead 114 includes a paddle body 510 extending between a distal end 506 and a proximal end 508. One or more electrode contacts 512 are disposed on at least one surface of the paddle body 510 and in electrical communication with the power source 116 via a lead body 514.

The electrode contacts 512 form the electrode array 140 arranged in an electrode array configuration, such as the electrode array configurations 500, 502, or 504. The electrode array configuration 500 includes eight electrode contacts 512 arranged in a four-by-two-by-two pattern. The electrode array configuration 502 includes twelve electrode contacts 512. In one implementation, the electrode contacts 512 are arranged in a six-by-three-by-three pattern in the electrode array configuration 502. Finally, the electrode array configuration 504 includes four electrodes arranged in a two-by-two pattern. It will be appreciated that other electrode array configurations are contemplated.

The paddle lead 114 may further have a variety of shapes and sizes to provide a thin, compact, low profile. For examples 600-604 of the dimensions of the paddle lead 114, reference is made to FIGS. 13A-13C. In one implementation, the paddle lead 114 includes a paddle body 610 extending between a distal end 606 and a proximal end 608. One or more electrode contacts 612 are disposed on at least one surface of the paddle body 610 and in electrical communication with the power source 116 via a lead body 614.

Each of the paddle leads 600-604 has a thin, compact, low profile. In one implementation, the paddle lead 600 has a length of approximately 2.8 to 3.5 inches, and the paddle body 610 has a width of approximately 2.0 to 3.4 inches. The paddle body 610 of the paddle lead 600 is sized to accommodate approximately eight electrode contacts 612. Similarly, the paddle leads 602 and 604 may be sized to accommodate approximately twelve electrode contacts 612. In one implementation, the paddle leads 604 and 606 have a length of approximately 3.0 to 3.8 inches, and the paddle body 610 of the paddle leads 602 and 604 has a width of approximately 2.3 to 3.4 inches. The paddle body 610 of the paddle lead 602 may taper in width distally to form a tapered distal tip.

It will be appreciated that the paddle leads 600-604 may have a variety of dimensions forming the thin, compact, low profile. For example, the paddle leads 600-604 may have a length of approximately 30 mm, 45 mm, 60 mm, 75 mm, 90 mm, or similar lengths. Further, the paddle body 610 and/or the lead body 614 may have a thickness ranging from approximately 0.020 inches to 0.055 inches.

The electrode contacts 612 may also be arranged in various electrode array configurations with different dimensions. The electrode array configurations may include any number of electrode contacts 612, for example, four, six, eight, twelve, sixteen, or the like. Each of the electrode contacts 612 may have a length ranging from approximately 2 mm to 4 mm. In some specific examples, the length of the electrode contacts 612 is approximately 1.5 mm, 2 mm, 2.5 mm, or 3 mm. The electrode contacts 612 may further have a longitudinal spacing ranging from approximately 1 mm to 4 mm depending on the electrode array configuration. For example, the longitudinal spacing may be approximately 1 mm, 2 mm, 3 mm, 4 mm, or the like. The electrode array configuration may have an array length ranging from approximately 10 mm to 24 mm, again depending on the electrode array configuration.

As can be understood from FIGS. 14A-14E, the paddle lead 114 may include a suture loop configurations (e.g., 700-708) for suture guided deployment and/or securing of the paddle lead 114. In one implementation, the paddle lead 114 includes a paddle body 714 extending between a distal end 710 and a proximal end 712. One or more electrode contacts 716 are disposed on at least one surface of the paddle body 714 and in electrical communication with the power source 116 via a lead body 720.

As shown in FIGS. 14A-14E, the suture loop configuration may have one or more suture holes 718 defined in or otherwise disposed along the paddle body 714, the lead body 720, and/or other areas of the paddle lead 114. For example, the suture loop configurations 700 and 702 may each include suture holes 718 defined in the paddle body 714. The suture loop configuration 700 includes a first set of suture holes 718 disposed near the distal end 710 of the paddle body 714 and a second set of suture holes 718 disposed near the proximal end 712 of the paddle body 714. The suture loop configuration 702 includes a first set of suture holes 718 disposed near the distal end 710 of the paddle body 714 and a second set of suture holes 718 disposed near a middle of the paddle body 714. In both of the suture loop configurations 700 and 702, the suture holes 718 are positioned so as not to interfere with the electrical pathways of the electrode contacts 716.

The suture loop configurations 704-708 include may each include suture holes 718 disposed along the lead body 720. In one implementation, the suture loop configurations 704-708 each include a first set of suture holes 718 disposed near the proximal end 712 of the paddle body 714 and a second set of suture holes 718 disposed proximal to the first set along the lead body 720.

Figure 15:
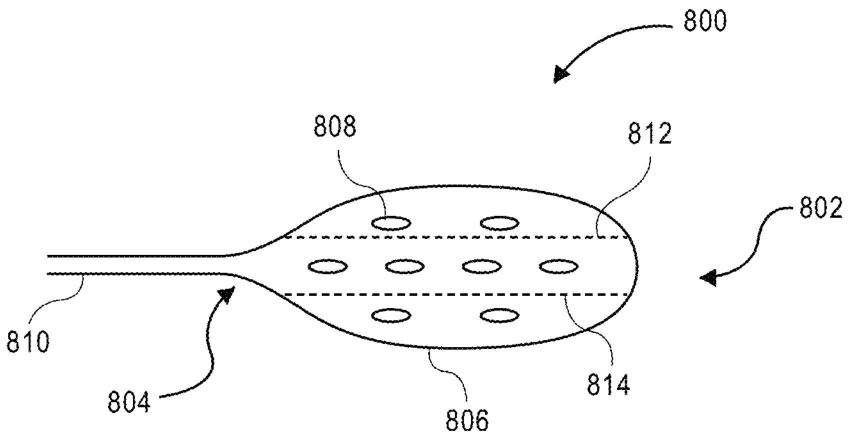
FIG. 15 illustrates an example paddle lead for DRG stimulation having a living hinge.

Turning to FIG. 15, in one implementation, the paddle lead 114 includes a living hinge 800 to hug or otherwise provide substantially continuous contact with the DRG 142. The paddle lead 114 includes a paddle body 806 extending between a distal end 802 and a proximal end 804. One or more electrode contacts 808 are disposed on at least one surface of the paddle body 806 and in electrical communication with the power source 116 via a lead body 810. The one or more electrode contacts 808 may be arranged in various electrode array configurations. For example, as shown in FIG. 15, the electrode contacts 808 are arranged in a 2D configuration pattern having a plurality of columns. Two of the electrode contacts 808 are arranged in a first column, four of the electrode contacts 808 are arranged in a second column adjacent the first column, and two of the electrode contacts 808 are arranged in a third column adjacent the second column.

In one implementation, the living hinge 800 includes a first hinge 812 and a second hinge 814, each extending a long a length of the paddle body 806 from the distal end 802 to the proximal end 804. The first hinge 812 is disposed between the first and second columns of electrode contacts 808, and the second hinge 814 is disposed between the second and third columns of electrode contacts 808. The first and second hinges 812 and 814 each form a joint in the paddle body 806 along which the paddle body 806 is bendable to navigate the anatomy of the target area in the patient 100 and to cradle the DRG 142.

Figure 16:
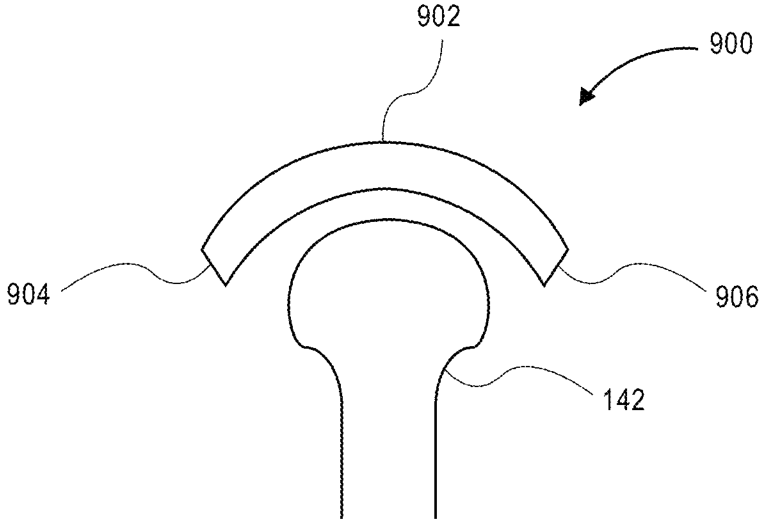
FIG. 16 depicts an example paddle lead for DRG stimulation with a paddle body contourable around the DRG.

As can be understood from FIG. 16, the paddle lead 114 may include a contourable paddle body 900. In one implementation, the contourable paddle body 900 extends along a curve from a first side 904 to a peak 902, and along a curve from a second side 906 to the peak 902. The shape formed by the contourable paddle body 900 mirrors a shape of the DRG 142 to facilitate contact by the electrode array 140 with the DRG 142 for stimulation. The shape of the contourable paddle body 900 may be maintained, for example, using wires or formable plates. Further, in some implementations, the shape of the contourable paddle body 900 may be manipulated during deployment to position the electrode array 140 for stimulation of the DRG 142.

Figure 17:
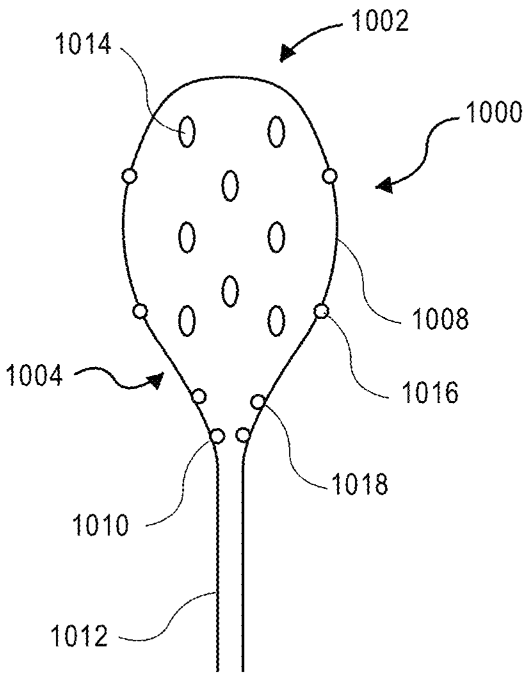
FIG. 17 shows an example paddle lead for DRG stimulation with an electrode configuration and a suture loop configuration.
Figure 18:
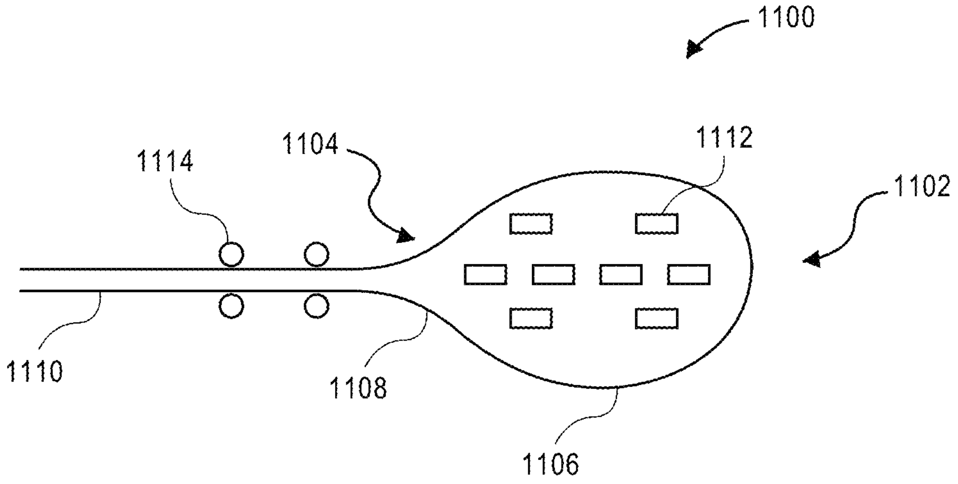
FIG. 18 illustrates an example paddle lead for DRG stimulation having a tapered neck.

FIG. 17 shows an example paddle lead 1000 for DRG stimulation with an electrode array configuration and a suture loop configuration. In one implementation, the paddle lead 1000 includes a paddle body 1008 extending between a distal end 1002 and a proximal end 1004. The paddle body 1008 tapers proximally into a neck 1010, and a lead body 1012 extends proximally from the neck 1010. One or more electrode contacts 1014 are disposed on at least one surface of the paddle body 1008 and in electrical communication with the power source 116 via a lead body 1012. The one or more electrode contacts 1014 may be arranged in various electrode array configurations. For example, the electrode array may include eight electrode contacts 1014 arranged in a 2D configuration with a three-by-two-by-three pattern.

For suture assisted deployment of the paddle lead 1000, in one implementation, a suture loop configuration has one or more suture holes 1016 defined in or disposed along the paddle body 1008, and one or more suture holes 1018 defined in or disposed along the neck 1010. For example, as shown in FIG. 15, the suture holes 1016 are defined along a periphery of the paddle body 1008 with a first set disposed distal to a middle of the paddle body 1008 and a second set disposed proximal to a middle of the paddle body 1008. The suture holes 1018 are defined in the neck 1010 with a first set disposed at a distal end of the neck 1010 near the proximal end 1004 of the paddle body 1008 and a second set disposed proximal to the first set near the lead body 1012. The paddle lead 1000 may be secured in the target area using one or more sutures extending through at least a portion of the suture loop configuration.

One or more portions of the paddle lead 114 may taper to facilitate deployment. As can be understood from FIG. 18, in one implementation, an example paddle lead 1100 includes a paddle body 1106 extending between a distal end 1102 and a proximal end 1104. The paddle body 1106 tapers proximally into a neck 1108, which tapers into a lead body 1110. One or more electrode contacts 1112 are disposed on at least one surface of the paddle body 1106 and in electrical communication with the power source 116 via a lead body 1110. In one implementation, a suture loop configuration has one or more suture holes 1114 defined in or disposed along the neck 1108 and/or the lead body 1110. The paddle lead 1100 may have a head diameter of approximately 0.055 inches providing a thin, compact, low profile.

Figure 19A:
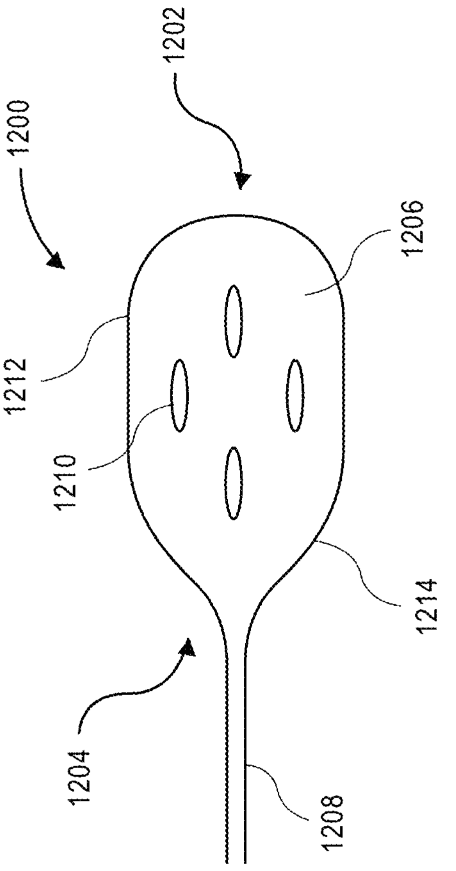
FIGS. 19A-19B show an example paddle lead for DRG stimulation with a paddle body contourable around the DRG.
Figure 19B:
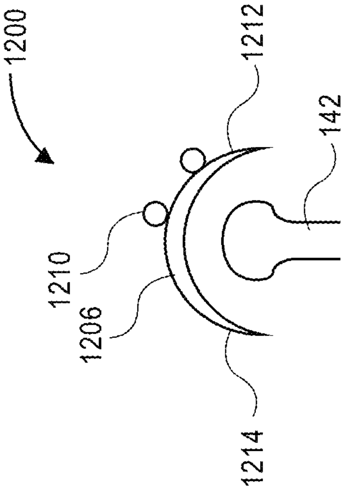

Another example paddle lead 1200 shown in FIGS. 19A-19B similarly has a thin, compact, low profile. The paddle lead 1200 includes a paddle body 1206 extending between a distal end 1202 and a proximal end 1204. One or more electrode contacts 1210 are disposed on at least one surface of the paddle body 1206 and in electrical communication with the power source 116 via a lead body 1208.

In one implementation, the paddle body 1206 is contourable, such that the paddle body 1206 may shaped to extend along a curve between a first side 1212 and a second side 1214. The shape formed by the paddle body 1206 mirrors a shape of the DRG 142 to facilitate contact by the electrode contacts 1210 with the DRG 142 for stimulation. The shape of the paddle body 1206 may be maintained, for example, using wires or formable plates. Further, in some implementations, the shape of the paddle body 1206 may be manipulated during deployment to position the electrode contacts 1210 for stimulation of the DRG 142.

Figure 20:
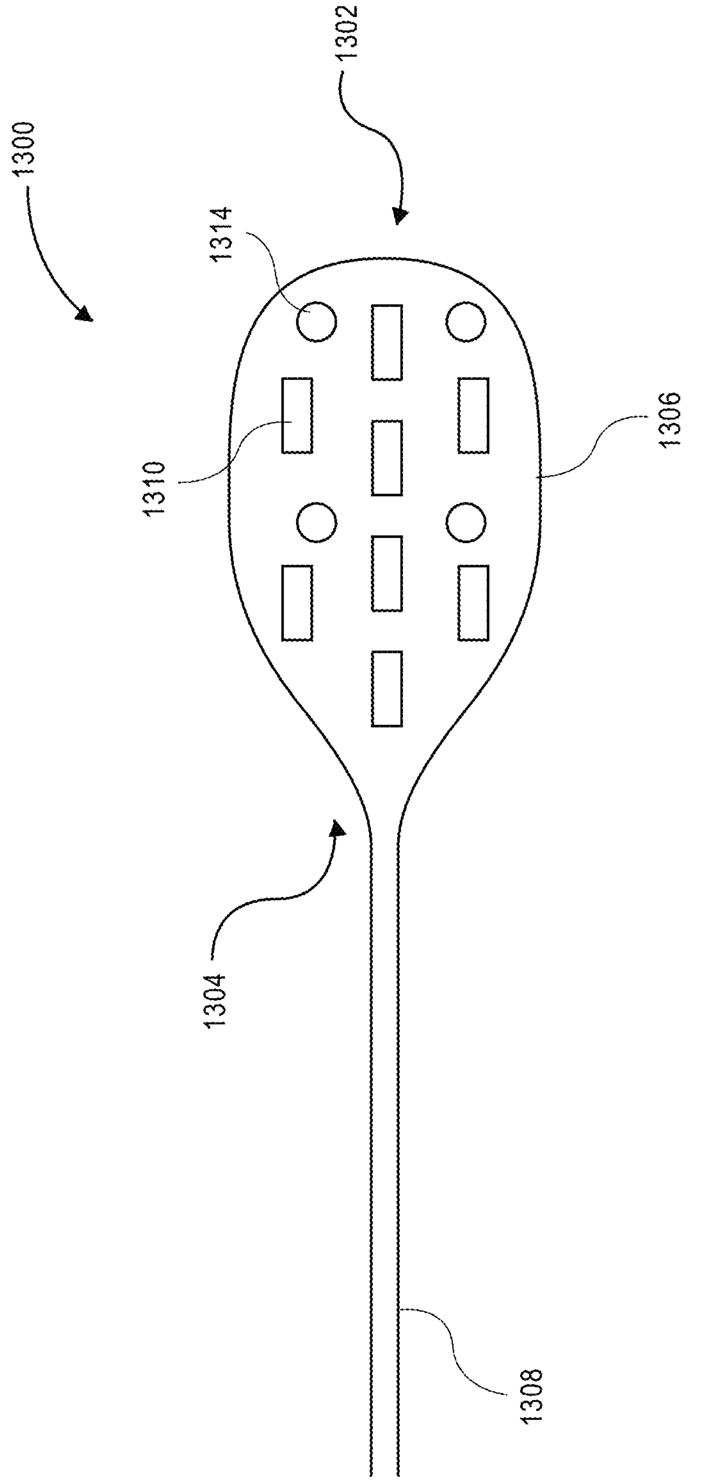
FIG. 20 depicts an example paddle lead for DRG stimulation with a suture loop configuration deployed on a paddle body.

As discussed herein, a suture loop configuration may be used to facilitate deployment. FIG. 20 depicts an example paddle lead 1300 for DRG stimulation with a suture loop configuration and one or more electrode contacts 1310 deployed on a paddle body 1306. The suture loop configuration has one or more suture holes 1312. For example, the suture loop configuration may include a first set of suture holes 1312 disposed near the distal end 1302 of the paddle body 1306 and a second set of suture holes 1312 disposed near a middle of the paddle body 1306, such that the suture holes 1312 are positioned so as not to interfere with the electrical pathways of the electrode contacts 1310. The paddle lead 1300 may be secured in the target area using one or more sutures extending through at least a portion of the suture loop configuration.

Figure 21A:
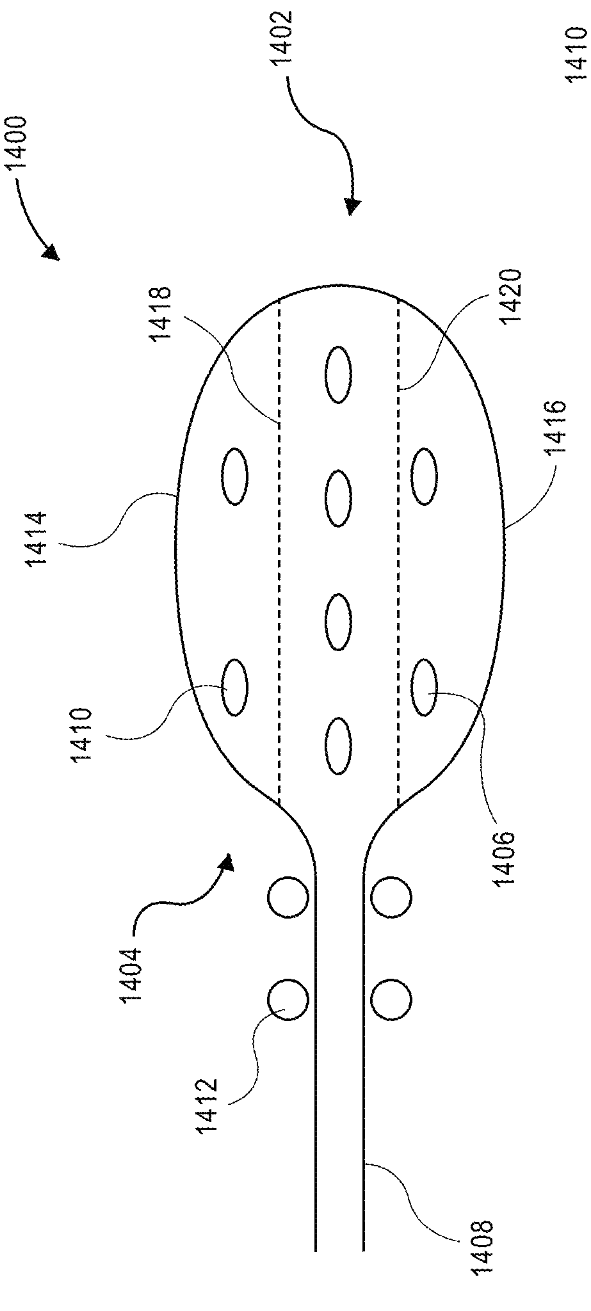
FIGS. 21A-21B illustrate an example paddle lead for DRG stimulation having a living hinge in a paddle body facilitating bending of the paddle body around the DRG.
Figure 21B:
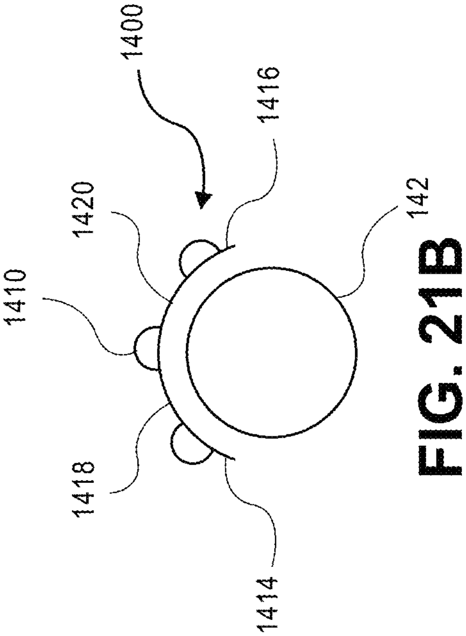

FIGS. 21A-21B illustrate another example paddle lead 1400 having a living hinge facilitating bending of a paddle body 1406 around the DRG 142. The paddle body 1406 extends between a distal end 1402 and a proximal end 1404, with a lead body 1408 extending from the proximal end 1404. In one implementation, a suture loop configuration having one or more suture holes 1412 is disposed along the lead body 1408.

One or more electrode contacts 1410 are disposed on at least one surface of the paddle body 1406 and in electrical communication with the power source 116 via a lead body 1408. The electrode contacts 1410 may have varying dimensions and spacing. For example, the electrode contacts 1410 may be approximately 2-3 mm in size with spacing of approximately 1.5-3 mm. The array formed by the electrode contacts 1410 may have a length of approximately 30-45 mm and a width of approximately 2-4 mm.

The electrode contacts 1410 may be arranged in various electrode array configurations. For example, as shown in FIG. 21A, the electrode contacts 1410 are arranged in a 2D configuration pattern having a plurality of columns. Two of the electrode contacts 1410 are arranged in a first column, four of the electrode contacts 1410 are arranged in a second column adjacent the first column, and two of the electrode contacts 1410 are arranged in a third column adjacent the second column.

In one implementation, the living hinge includes a first hinge 1418 and a second hinge 1420, each extending a long a length of the paddle body 1406 from the distal end 1402 to the proximal end 1404. The first hinge 1418 is disposed between the first and second columns of electrode contacts 1410, and the second hinge 1420 is disposed between the second and third columns of electrode contacts 1410. The first and second hinges 1418 and 1420 each form a joint in the paddle body 1406 along which the paddle body 1406 is bendable to navigate the anatomy of the target area in the patient 100 and to cradle the DRG 142. More particularly, the paddle body 1406 extends from a first side 1414 to the first hinge 1418 and from a second side 1416 to the second hinge 1420, thereby bending around a contour of the DRG 142 as shown in FIG. 21B.

Figure 22:
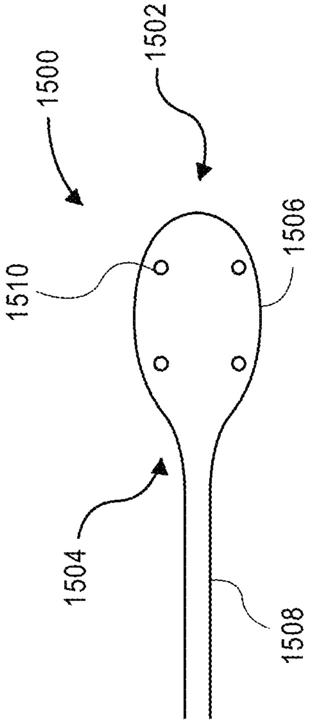
FIGS. 22-24 show various examples of paddle leads for DRG stimulation having a tapered paddle body.
Figure 23:
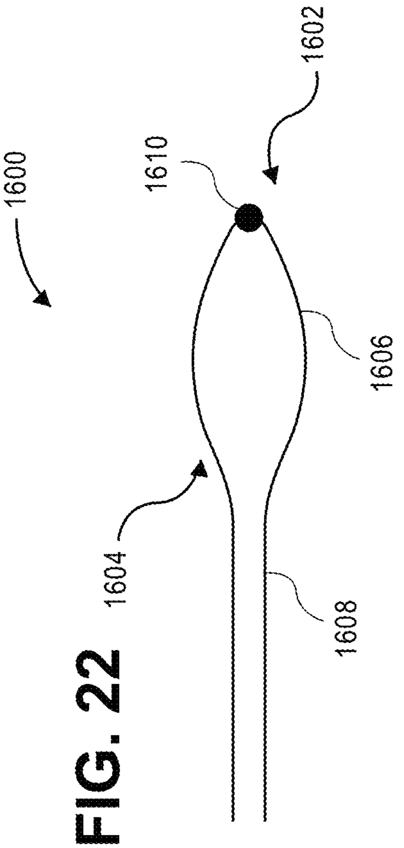
Figure 24:
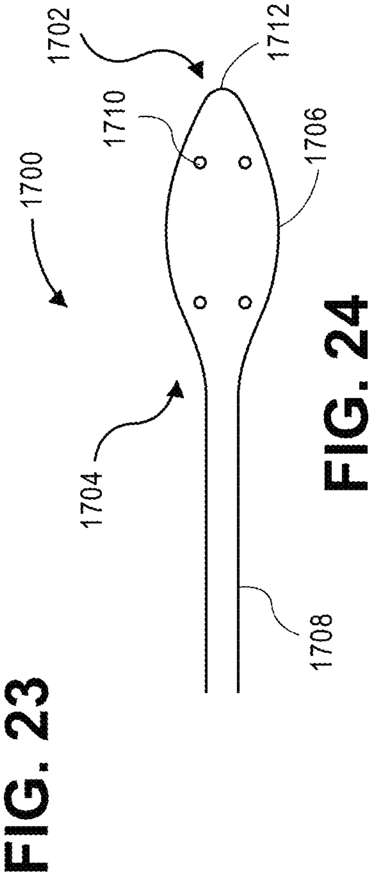

As described herein, the paddle lead 114 may include a tapered end to advance surgical placement. FIGS. 22-24 show various examples of paddle leads 1500, 1600, and 1700 including such features. Turning first to FIG. 22, in one implementation, the paddle lead 1500 includes a paddle body 1506 extending between a distal end 1502 and a proximal end 1504. A lead body 1508 extends from the proximal end 1504.

In one implementation, the paddle body 1506 tapers distally in width towards the distal end 1502 to form a tapered distal tip. The tapered distal tip may have a variety of shapes. For example, the tapered distal tip may have a rounded edge, such that the width of the paddle body 1506 tapers smoothly along a curve toward the distal end 1502. The paddle body 1506 may further taper proximally at the proximal end 1504 towards the lead body 1508.

To further assist surgical placement, the paddle body 1506 may include a suture loop configuration with one or more suture holes 1510 defined therein. In one implementation, a first set of the suture holes 1510 is disposed on a periphery of the paddle body 1506 where the width begins to taper into the tapered distal tip. A second set of the suture holes 1510 is disposed on the periphery of the paddle body 1506 proximal to the first set of the suture holes 1510. In one implementation, the second set of the suture holes 1510 is disposed at the proximal end 1504 where the width begins to taper proximally to connect with the lead body 1508.

Turning next to FIG. 23, in one implementation, the paddle lead 1600 includes a paddle body 1606 extending between a distal end 1602 and a proximal end 1604. A lead body 1608 extends from the proximal end 1604. In one implementation, the paddle body 1606 tapers distally in width towards the distal end 1602 to form a tapered distal tip. As discussed above, the tapered distal tip may have a variety of shapes. For example, the tapered distal tip may have a pointed edge as shown in FIG. 23, such that the width of the paddle body 1606 tapers along an angle toward the distal end 1602. The paddle body 1606 may further taper proximally at the proximal end 1604 towards the lead body 1608. To further assist surgical placement, the paddle body 1606 may include a suture loop configuration with one or more suture holes 1610 defined therein. In one implementation, the suture loop configuration includes one suture hole 1610 disposed at a distal edge of the tapered distal tip.

Similarly, turning to FIG. 24, in one implementation, the paddle lead 1700 includes a paddle body 1706 extending between a distal end 1702 and a proximal end 1704. A lead body 1708 extends from the proximal end 1704. In one implementation, the paddle body 1706 tapers distally in width towards the distal end 1702 to form a tapered distal tip. As shown in FIG. 24, the tapered distal tip may have a pointed edge, such that the width of the paddle body 1706 tapers along an angle toward the distal end 1702. The paddle body 1706 may further taper proximally at the proximal end 1704 towards the lead body 1708 along an angle.

To further assist surgical placement, the paddle body 1706 may include a suture loop configuration with one or more suture holes 1710 defined therein. In one implementation, the suture loop configuration includes a first set of the suture holes 1710 is disposed on a periphery of the paddle body 1706 where the width begins to taper into the tapered distal tip. A second set of the suture holes 1710 is disposed on the periphery of the paddle body 1706 proximal to the first set of the suture holes 1710. In one implementation, the second set of the suture holes 1710 is disposed at the proximal end 1704 where the width begins to taper proximally to connect with the lead body 1708.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. A method for electrically stimulating a dorsal root ganglion, the method comprising:

identifying a target area below vertebral lamina dorsal to the dorsal root ganglion, the dorsal root ganglion being posterior to a spinal cord of a patient;

removing lateral laminar and ligament by performing a medial laminectomy, removal of the lateral laminar and ligament providing access to foraminal space;

deploying a paddle lead into neuroforamen dorsal to the dorsal root ganglion with the foraminal space accessed using a minimally invasive surgical approach, the paddle lead having a lead body and a paddle body extending between a proximal end and a distal end, the lead body extending from the proximal end of the paddle body, the paddle body including an electrode array disposed on at least one surface and a living hinge formed by the paddle body extending from a first side to a first hinge and from a second side to a second hinge, the electrode array having one or more electrode contacts arranged in an electrode array configuration; and surgically placing the paddle body of the paddle lead in a target orientation within the target area over the dorsal root ganglion using a tapered distal tip and suture guided deployment, the target orientation positioning the electrode array for electrical stimulation of the dorsal root ganglion, the electrical stimulation being applied to the dorsal root ganglion from an implantable pulse generator using the electrode array of the paddle lead to treat chronic pain of the patient.

2. The method of claim 1, wherein the paddle body is deployed into one of lumbar or thoracic neuroformen caudal to pedicles.

3. The method of claim 1, wherein the paddle lead is deployed into the foraminal space using a delivery tool having a sheath with a spatula shaped distal tip.

4. The method of claim 1, wherein the tapered distal tip has a rounded shape or a pointed shape.

5. The method of claim 1, wherein the target orientation further includes the paddle body cradling the dorsal root ganglion using the living hinge.

6. The method of claim 5, wherein the first hinge and the second hinge both form a joint configured to bend the paddle body along a contour to cradle the dorsal root ganglion.

7. The method of claim 1, wherein guiding the paddle lead using one or more suture holes disposed along at least one of the paddle body or the lead body.

8. The method of claim 7, wherein the one or more suture holes are disposed on the paddle body relative to electrical pathways of the one or more electrode contacts.

9. The method of claim 7, wherein the one or more suture holes form a suture loop configuration.

10. The method of claim 9, wherein the suture loop configuration includes a first set of suture holes and a second set of suture holes, wherein the first set of suture holes is disposed at the distal end of the paddle body and the second set of suture holes is disposed at the proximal end of the paddle body.

11. The method of claim 1, wherein the tapered distal tip formed by the paddle body tapers in width towards the distal end.

12. The method of claim 1, wherein the electrode array configuration includes a two-dimensional electrode array configuration forming an asymmetrical paddle lead, the target orientation including the electrical stimulation being focused in a single direction within the target area.

13. The method of claim 12, wherein the single direction is away from scar tissue in the target area to overcome stimulation loss caused by the scar tissue.

14. The method of claim 12, wherein the two-dimensional electrode array configuration includes a four-by-two-by-two pattern; a six-by-three-by-three pattern; or a two-by-two pattern.

15. The method of claim 12, wherein the two-dimensional electrode array configuration includes the one or more electrode contacts arranged in a nonlinear pattern with a plurality of columns.

16. The method of claim 15, wherein the plurality of columns includes a first column, a second column, and a third column, the paddle body cradling the dorsal root ganglion using the living hinge, the living hinge formed by the paddle body extending from the first side to the first hinge and from the second side to the second hinge, the first hinge and the second hinge both form a joint configured to bend the paddle body along a contour to cradle the dorsal root ganglion, the first hinge being disposed between the first column and the second column, and the second hinge being disposed between the second column and the third column.

17. The method of claim 1, wherein the electrode array is configured for at least one of high frequency or burst stimulation patterns.

18. The method of claim 1, wherein the electrode array has a length ranging from thirty to forty-five millimeters and a width ranging from two to four millimeters.

19. A method for electrically stimulating a dorsal root ganglion, the method comprising:

identifying a target area below vertebral lamina dorsal to the dorsal root ganglion, the dorsal root ganglion being posterior to a spinal cord of a patient;

removing lateral laminar and ligament by performing a medial laminectomy, removal of the lateral laminar and ligament providing access to foraminal space;

deploying a paddle lead into neuroforamen dorsal to the dorsal root ganglion with the foraminal space accessed using a minimally invasive surgical approach, the paddle lead having a lead body and a paddle body extending between a proximal end and a distal end, the lead body extending from the proximal end of the paddle body, the paddle body including an electrode array having one or more electrode contacts and a living hinge formed by the paddle body extending from a first side to a first hinge and from a second side to a second hinge;

surgically placing the paddle body of the paddle lead in a target orientation within the target area over the dorsal root ganglion using suture guided deployment, the target orientation positioning the electrode array for electrical stimulation of the dorsal root ganglion; and applying the electrical stimulation to the dorsal root ganglion from an implantable pulse generator using the one or more electrode contacts to treat chronic pain of the patient.

20. A device for electrically stimulating a dorsal root ganglion, the device comprising:

a paddle lead having a lead body and a paddle body extending between a proximal end and a distal end, the lead body extending from the proximal end of the paddle body, the paddle body including an electrode array having one or more electrode contacts, the paddle lead including one or more suture holes disposed along at least one of the paddle body or the lead body, the paddle body including an electrode array disposed on at least one surface and a living hinge formed by the paddle body extending from a first side to a first hinge and from a second side to a second hinge; and a tapered distal tip, wherein the paddle body tapers in width towards the distal end.

* * * * *